(12) United States Patent
Li et al.

(10) Patent No.: US 11,738,051 B2
(45) Date of Patent: Aug. 29, 2023

(54) NUCLEOTIDE SEQUENCES FOR ENCODING CAR, ROBO1 CAR-NK CELLS OF EXPRESSING THE CAR, AND PREPARATION AND APPLICATION THEREOF

(71) Applicant: Asclepius (Suzhou) Technology Company Group Co., Ltd., Suzhou (CN)

(72) Inventors: Huashun Li, Suzhou (CN); Kunkun Han, Suzhou (CN); Baolei Wang, Suzhou (CN); Baoyong Ren, Suzhou (CN)

(73) Assignee: ASCLEPIUS (SUZHOU) TECHNOLOGY COMPANY GROUP CO., LTD., Suzhou (CN)

( * ) Notice: Subject to any disclaimer, the term of this patent is extended or adjusted under 35 U.S.C. 154(b) by 463 days.

(21) Appl. No.: 16/893,989

(22) Filed: Jun. 5, 2020

(65) Prior Publication Data
US 2020/0289573 A1    Sep. 17, 2020

Related U.S. Application Data

(63) Continuation of application No. PCT/CN2018/117897, filed on Nov. 28, 2018.

(30) Foreign Application Priority Data

Dec. 6, 2017 (CN) .......................... 201711276303.6

(51) Int. Cl.
| | |
|---|---|
| A61K 35/17 | (2015.01) |
| A61P 35/00 | (2006.01) |
| C07K 14/725 | (2006.01) |
| C07K 14/705 | (2006.01) |
| C12N 15/62 | (2006.01) |

(52) U.S. Cl.
CPC .............. *A61K 35/17* (2013.01); *A61P 35/00* (2018.01); *C07K 14/7051* (2013.01); *C07K 14/70517* (2013.01); *C07K 14/70578* (2013.01); *C12N 15/62* (2013.01)

(58) Field of Classification Search
CPC ................................ A61K 35/17; C12N 15/62
See application file for complete search history.

(56) References Cited

FOREIGN PATENT DOCUMENTS

| | | | |
|---|---|---|---|
| CN | 105907719 | A | 8/2016 |
| CN | 106220736 | A | 12/2016 |
| CN | 106459916 | A | 2/2017 |
| CN | 107034237 | A | 8/2017 |
| CN | 107106611 | A | 8/2017 |
| CN | 108977453 | A | 12/2018 |
| WO | 2013051718 | A1 | 4/2013 |
| WO | 2015095895 | A8 | 6/2015 |
| WO | 2016/069647 | A1 | 5/2016 |
| WO | 2016069647 | A1 | 5/2016 |
| WO | 2016201251 | A1 | 12/2016 |
| WO | 2016201300 | A1 | 12/2016 |
| WO | 2016208754 | A1 | 12/2016 |
| WO | 2017/181552 | A1 | 10/2017 |
| WO | 2017181552 | A1 | 10/2017 |

OTHER PUBLICATIONS

EPO, Munich, Germany, Date: Dec. 18, 2020, Application No. PCT/CN2018117897, Applicant: Asclepius (Suzhou) Technology Company Group Co., Ltd., Communication Pursuant To Rule 164(1) EPC, Partial Supplementary European Search Report.
Japanese Patent Application No. 2020-549850, Notice of Reasons for Refusal, dated Nov. 12, 2021.
Daisuke Kanda, Brief Summary of the sixteenth Annual Protein Science Association, 2016, p. 114.
Yuan Hu, Zhi-gang Tian, and Cai Zhang, Chimeric antigen receptor (CAR)-transduced natural killer cells in tumor immunotherapy, Acta Pharmacologica Sinica (2018) 39: 167-176; doi: 10.1038/aps. 2017.125; published online Sep. 7, 2017.
European Patent Office, Extended European Search Report and the European Search Opinion, dated Feb. 15, 2021, EPO Application No. 18886924.2, International Application No. PCT/CN2018117897, Applicant: Asclepius (Suzhou) Technology Company Group Co., Ltd.
Maelig G. Morvan, et al., "NK Cells and Cancer: You Can Teach Innate Cells New Tricks," Nature Reviews Cancer, vol. 6, No. 1, Published: Jan. 1, 2016, ISSN: 1474-175X.
Ning Xia, et al., "Robo1-specific CAR-NK Immunotherapy Enhances Efficacy of I Seed Brachytherapy in an Orthotopic Mouse Model of Human Pancreatic Carcinoma," Anticancer Research, vol. 39, pp. 5919-5925, Published: Oct. 11, 2019.
Chimeric antigen receptor (CAR)-transduced natural killer cells in tumor immunotherapy, Yuan Hu, Zhi-gang Tian, Cai Zhang, Acta Pharmacologica Sinica (2018) 39: 167-176 doi: 10.1038/aps.2017. 125 published online Sep. 7, 2017.

(Continued)

*Primary Examiner* — Elly-Gerald Stoica
(74) *Attorney, Agent, or Firm* — Flener IP & Business Law; Zareefa B. Flener

(57) ABSTRACT

The present invention provides a nucleotide sequence for encoding CAR, a ROBO1 CAR-NK cell of expressing the CAR, and preparation and application thereof. The ROBO1 CAR-NK cell provided by the present invention can specifically kill tumor cells by using ROBO1 antibody for the construction of CAR-NK cells and using ROBO1 molecules as target antigens. It can be used as a therapeutic agent for tumor diseases, for the treatment of tumor with highly expressing of ROBO1, without harmful phenomena such as cytokine release syndrome, thus providing new treatments for the tumors which are ineffective in traditional surgery, chemotherapy and radiotherapy. It has lower toxicity, higher safety and better specific lysis activity compared with ROBO1 CAR-T cell.

11 Claims, 13 Drawing Sheets
Specification includes a Sequence Listing.

(56) References Cited

OTHER PUBLICATIONS

Notice of Reasons for Refusal, Japanese Patent Application No. 2020-549850, Reiwa 3 (Jun. 9, 2021).
International Search Report, PCT/CN2018/117897, dated Feb. 15, 2019.
Patent Cooperation Treaty, International Preliminary Report on Patentability, PCT/CN2018/117897, dated Jun. 9, 2020, Asclepius (Suzhou) Technology Company Group Co., Ltd.
Natl Med J China, Mar. 20, 2018, vol. 98, No. 11, Killing Effect of Robo1 Targeted Chimeric ANtigen Receptor Modified NK92 Cells Against Glioma and Neuroblastoma Cells, Qu Yue, Bi Jianzhong, Department of Neural Medicine, Second Hospital of Shandong University, Jinan 25033, China. Abstract in English.
Notification to Grant Patent Right for Invention, Application No. or Publication Issue No. 201811394153.3, Asclepius (Suzhou) Biotechnology Co., Ltd.
The State Intellectual Property Office of People's Republic of China, First Office Action, Application No. or Publication Issue No. 201811394153.3, Asclepius (Suzhou) Biotechnology Co., Ltd.

Before therapy
2017.5.27

After therapy
2017.6.15

After therapy
2017.7.14

SEQUENCE LISTING

```
<160> NUMBER OF SEQ ID NOS: 4

<210> SEQ ID NO 1
<211> LENGTH: 480
<212> TYPE: PRT
<213> ORGANISM: Artificial Sequence
<220> FEATURE:
```

-continued

<223> OTHER INFORMATION: ScFV(Anti ROBO1-FN3)- CD8-4-1BB-CD3??

<400> SEQUENCE: 1

```
Met Ala Leu Pro Val Thr Ala Leu Leu Leu Pro Leu Ala Leu Leu Leu
1               5                   10                  15

His Ala Ala Arg Pro Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Phe Leu Asn Trp Tyr Gln Gln Lys Pro Asp Gly Thr Val
50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Phe Ser Leu Thr Ile Ser
                85                  90                  95

Lys Leu Glu Gln Glu Asp Ile Ala Thr Tyr Phe Cys Gln Gln Gly Asn
            100                 105                 110

Thr Leu Pro Leu Thr Phe Gly Ala Gly Thr Lys Leu Glu Leu Lys Gly
        115                 120                 125

Gly Gly Gly Ser Gly Gly Gly Ser Gly Gly Gly Ser Leu Gln
130                 135                 140

Gln Ser Gly Pro Glu Leu Val Lys Pro Gly Ala Ser Val Lys Ile Ser
145                 150                 155                 160

Cys Lys Ala Ser Gly Tyr Thr Phe Thr Asp Tyr Tyr Met Asn Trp Val
                165                 170                 175

Lys Leu Ser His Gly Lys Ser Leu Glu Trp Ile Gly Asp Ile Val Pro
            180                 185                 190

Asn Asn Gly Asp Thr Thr Tyr Asn Gln Asn Phe Arg Gly Lys Ala Thr
        195                 200                 205

Leu Thr Val Asp Lys Ser Ser Ser Thr Ala Tyr Met Glu Leu Arg Ser
210                 215                 220

Leu Thr Ser Glu Asp Ser Ala Val Tyr Tyr Cys Ala Arg Phe Ser Asn
225                 230                 235                 240

Tyr Val Tyr Pro Phe Asp Tyr Trp Gly Gln Gly Thr Thr Ile Thr Val
                245                 250                 255

Ser Thr Thr Thr Pro Ala Pro Arg Pro Pro Thr Pro Ala Pro Thr Ile
            260                 265                 270

Ala Ser Gln Pro Leu Ser Leu Arg Pro Glu Ala Cys Arg Pro Ala Ala
        275                 280                 285

Gly Gly Ala Val His Thr Arg Gly Leu Asp Phe Ala Cys Asp Ile Tyr
290                 295                 300

Ile Trp Ala Pro Leu Ala Gly Thr Cys Gly Val Leu Leu Leu Ser Leu
305                 310                 315                 320

Val Ile Thr Leu Tyr Cys Lys Arg Gly Arg Lys Lys Leu Leu Tyr Ile
                325                 330                 335

Phe Lys Gln Pro Phe Met Arg Pro Val Gln Thr Thr Gln Glu Glu Asp
            340                 345                 350

Gly Cys Ser Cys Arg Phe Pro Glu Glu Glu Glu Gly Gly Cys Glu Leu
        355                 360                 365

Arg Val Lys Phe Ser Arg Ser Ala Asp Ala Pro Ala Tyr Gln Gln Gly
370                 375                 380

Gln Asn Gln Leu Tyr Asn Glu Leu Asn Leu Gly Arg Arg Glu Glu Tyr
385                 390                 395                 400
```

```
Asp Val Leu Asp Lys Arg Arg Gly Arg Asp Pro Glu Met Gly Gly Lys
                405                 410                 415

Pro Arg Arg Lys Asn Pro Gln Glu Gly Leu Tyr Asn Glu Leu Gln Lys
            420                 425                 430

Asp Lys Met Ala Glu Ala Tyr Ser Glu Ile Gly Met Lys Gly Glu Arg
        435                 440                 445

Arg Arg Gly Lys Gly His Asp Gly Leu Tyr Gln Gly Leu Ser Thr Ala
    450                 455                 460

Thr Lys Asp Thr Tyr Asp Ala Leu His Met Gln Ala Leu Pro Pro Arg
465                 470                 475                 480

<210> SEQ ID NO 2
<211> LENGTH: 1440
<212> TYPE: DNA
<213> ORGANISM: Artificial Sequence
<220> FEATURE:
<223> OTHER INFORMATION: ScFV(Anti ROBO1-FN3)- CD8-4-1BB-CD3ζζ

<400> SEQUENCE: 2
atggccctgc ctgtgacagc cctgctgctg cctctggctc tgctgctgca tgccgctaga      60
cccatccaga tgacacagac tacatcctcc ctgtctgcct ctctgggaga cagagtcacc     120
atcagttgca gggcaagtca ggacattagc aattttttaa actggtatca gcagaaacca     180
gatggaactg ttaaactcct gatctactac acatcaagat acattctgg agtcccatca     240 aggttcagtg gcagtgggtc tggaacagat ttttctctca ccattagcaa actggagcaa     300
gaagatattg ccacttactt tgccaacag ggtaatacgc ttccacttac gttcggcgct     360
gggacaaagt tggaacttaa aggtggtggt ggttctggcg gcggcggctc cggaggagga     420
ggatcgctgc aacagtctgg acctgagttg gtgaagcctg ggcttcagt gaagatttcc     480 tgcaaggctt ctggatacac attcactgac tactacatga attgggtgaa gcttagccat     540
ggaaagagcc ttgagtggat tggagatatt gttcctaaca atggtgatac tacttacaac     600
cagaatttca gaggcaaggc cacattgact gtagacaagt cctccagcac agcctacatg     660
gagctccgca gcctgacatc tgaggactct gcagtctatt actgtgcaag attcagtaat     720
tacgtttacc cttttgacta ctggggccaa ggcaccacta tcacagtctc caccacgacg     780
ccagcgccgc gaccaccaac accggcgccc accatcgcgt cgcagcccct gtccctgcgc     840
ccagaggcgt gccggccagc ggcggggggc gcagtgcaca cgagggggct ggacttcgcc     900
tgtgatatct acatctgggc gcccttggcc gggacttgtg ggtccttct cctgtcactg     960 gttatcaccc tttactgcaa acggggcaga aagaaactcc tgtatatatt caaacaacca    1020
tttatgagac cagtacaaac tactcaagag gaagatggct gtagctgccg atttccagaa    1080
gaagaagaag aggatgtga actgagagtg aagttcagca ggagcgcaga cgccccgcg    1140 taccagcagg gccagaacca gctctataac gagctcaatc taggacgaag agaggagtac    1200
gatgttttgg acaagagacg tggccgggac cctgagatgg ggggaaagcc agaaggaag    1260 aaccctcagg aaggcctgta caatgaactg cagaaagata gatggcgga ggcctacagt    1320 gagattggga tgaaaggcga gcgcggagg ggcaagggc acgatggcct ttaccagggt    1380
ctcagtacag ccaccaagga cacctacgac gcccttcaca tgcaggccct gcccctcgc    1440

<210> SEQ ID NO 3
<211> LENGTH: 480
<212> TYPE: PRT
<213> ORGANISM: Artificial Sequence
<220> FEATURE:
```

<223> OTHER INFORMATION: Mutant ScFV(Anti ROBO1-FN3)- CD8-4-1BB-CD3??

<400> SEQUENCE: 3

```
Met Ala Leu Pro Val Thr Ala Leu Leu Leu Pro Leu Ala Leu Leu Leu
1               5                   10                  15

His Ala Ala Arg Pro Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Phe Leu Asn Trp Tyr Gln Gln Lys Pro Asp Gly Thr Val
    50                  55                  60

Lys Leu Leu Ile Tyr Ala Thr Ser Arg Leu His Ser Gly Val Pro Ser
65                  70                  75                  80

Arg Phe Ser Gly Ser Gly Ser Gly Thr Asp Phe Ser Leu Thr Ile Ser
                85                  90                  95

Lys Leu Glu Gln Glu Asp Ile Ala Thr Tyr Phe Cys Gln Gln Gly Asn
            100                 105                 110

Thr Leu Pro Leu Thr Phe Gly Ala Gly Thr Lys Leu Glu Leu Lys Gly
        115                 120                 125

Gly Gly Gly Ser Gly Gly Gly Ser Gly Gly Gly Ser Leu Gln
130                 135                 140

Gln Ser Gly Pro Glu Leu Val Lys Pro Gly Ala Ser Val Lys Ile Ser
145                 150                 155                 160

Cys Lys Ala Ser Gly Tyr Thr Phe Thr Asp Tyr Tyr Met Asn Trp Val
                165                 170                 175

Lys Leu Ser His Gly Lys Ser Leu Glu Trp Ile Gly Asp Ile Val Pro
            180                 185                 190

Asn Asn Gly Asp Thr Thr Tyr Asn Gln Asn Phe Arg Gly Lys Ala Thr
        195                 200                 205

Leu Thr Val Asp Lys Ser Ser Ser Thr Ala Tyr Met Glu Leu Arg Ser
210                 215                 220

Leu Thr Ser Glu Asp Ser Ala Val Tyr Tyr Cys Ala Arg Phe Ser Asn
225                 230                 235                 240

Tyr Val Tyr Pro Phe Asp Tyr Trp Gly Gln Gly Thr Thr Ile Thr Val
                245                 250                 255

Ser Thr Thr Thr Pro Ala Pro Arg Pro Pro Thr Pro Ala Pro Thr Ile
            260                 265                 270

Ala Ser Gln Pro Leu Ser Leu Arg Pro Glu Ala Cys Arg Pro Ala Ala
        275                 280                 285

Gly Gly Ala Val His Thr Arg Gly Leu Asp Phe Ala Cys Asp Ile Tyr
290                 295                 300

Ile Trp Ala Pro Leu Ala Gly Thr Cys Gly Val Leu Leu Leu Ser Leu
305                 310                 315                 320

Val Ile Thr Leu Tyr Cys Lys Arg Gly Arg Lys Lys Leu Leu Tyr Ile
                325                 330                 335

Phe Lys Gln Pro Phe Met Arg Pro Val Gln Thr Thr Gln Glu Glu Asp
            340                 345                 350

Gly Cys Ser Cys Arg Phe Pro Glu Glu Glu Glu Gly Gly Cys Glu Leu
        355                 360                 365

Arg Val Lys Phe Ser Arg Ser Ala Asp Ala Pro Ala Tyr Gln Gln Gly
370                 375                 380

Gln Asn Gln Leu Tyr Asn Glu Leu Asn Leu Gly Arg Arg Glu Glu Tyr
385                 390                 395                 400
```

```
Asp Val Leu Asp Lys Arg Arg Gly Arg Asp Pro Glu Met Gly Gly Lys
            405                 410                 415

Pro Arg Arg Lys Asn Pro Gln Glu Gly Leu Tyr Asn Glu Leu Gln Lys
            420                 425                 430

Asp Lys Met Ala Glu Ala Tyr Ser Glu Ile Gly Met Lys Gly Glu Arg
            435                 440                 445

Arg Arg Gly Lys Gly His Asp Gly Leu Tyr Gln Gly Leu Ser Thr Ala
            450                 455                 460

Thr Lys Asp Thr Tyr Asp Ala Leu His Met Gln Ala Leu Pro Pro Arg
465                 470                 475                 480

<210> SEQ ID NO 4
<211> LENGTH: 1440
<212> TYPE: DNA
<213> ORGANISM: Artificial Sequence
<220> FEATURE:
<223> OTHER INFORMATION: Mutant ScFV(Anti ROBO1-FN3)- CD8-4-1BB-CD3??

<400> SEQUENCE: 4
atggccctgc ctgtgacagc cctgctgctg cctctggctc tgctgctgca tgccgctaga      60
cccatccaga tgacacagac tacatcctcc ctgtctgcct ctctgggaga cagagtcacc     120
atcagttgca gggcaagtca ggacattagc aattttttaa actggtatca gcagaaacca     180
gatggaactg ttaaactcct gatctacgcc acatcaagat acattctgg agtcccatca      240 aggttcagtg gcagtgggtc tggaacagat ttttctctca ccattagcaa actggagcaa     300
gaagatattg ccacttactt ttgccaacag gtaatacgc ttccacttac gttcggcgct      360
gggacaaagt tggaacttaa aggtggtggt ggttctggcg gcggcggctc cggaggagga     420
ggatcgctgc aacagtctgg acctgagttg gtgaagcctg ggcttcagt gaagatttcc      480 tgcaaggctt ctggatacac attcactgac tactacatga attgggtgaa gcttagccat     540
ggaaagagcc ttgagtggat tggagatatt gttcctaaca atggtgatac tacttacaac     600
cagaatttca gaggcaaggc cacattgact gtagacaagt cctccagcac agcctacatg     660
gagctccgca gcctgacatc tgaggactct gcagtctatt actgtgcaag attcagtaat     720
tacgtttacc cttttgacta ctggggccaa ggcaccacta tcacagtctc caccacgacg     780
ccagcgccgc gaccaccaac accggcgccc accatcgcgt cgcagcccct gtcctgcgc     840 ccagaggcgt gccggccagc ggcggggggc gcagtgcaca cgagggggct ggacttcgcc     900
tgtgatatct acatctgggc gcccttggcc gggacttgtg ggtccttct cctgtcactg     960 gttatcaccc tttactgcaa acggggcaga aagaaactcc tgtatatatt caaacaacca    1020
tttatgagac cagtacaaac tactcaagag gaagatggct gtagctgccg atttccagaa    1080
gaagaagaag aggatgtgaa actgagagtg aagttcagca ggagcgcaga cgccccgcg     1140 taccagcagg gccagaacca gctctataac gagctcaatc taggacgaag agaggagtac    1200
gatgttttgg acaagagacg tggccgggac cctgagatgg ggggaaagcc gagaaggaag    1260
aaccctcagg aaggcctgta caatgaactg cagaaagata gatggcgga ggcctacagt     1320 gagattggga tgaaaggcga gcgccggagg ggcaagggc acgatggcct ttaccagggt    1380
ctcagtacag ccaccaagga cacctacgac gcccttcaca tgcaggccct gccccctcgc    1440
```

NUCLEOTIDE SEQUENCES FOR ENCODING CAR, ROBO1 CAR-NK CELLS OF EXPRESSING THE CAR, AND PREPARATION AND APPLICATION THEREOF

CROSS-REFERENCE TO RELATED APPLICATION

This application is a continuation application of International patent application No. PCT/CN2018/117897, filed on Nov. 28, 2018, which claims priority to Chinese patent application No. CN201711276303.6, filed on Dec. 6, 2017. All of the aforementioned patent applications are hereby incorporated by reference in their entireties.

TECHNICAL FIELD

The present invention relates to the field of biological medicine, in particular to a nucleotide sequence for encoding CAR, a ROBO1 CAR-NK cell of expressing the CAR, and preparation and application thereof.

BACKGROUND

Breast is composed of skin, fibrous tissue, mammary glands and fat. Breast cancer is a malignant tumor that occurs in the epithelium of the mammary glands. 99% of breast cancer occurs in women, and only 1% in men.

Breast is not an important organ in maintaining human life. Breast cancer in situ is not fatal. However, the breast cancer cells lost their normal character, and are loosely connected with the surrounding cells, easy to fall off. Once the cancer cells are fallen off, the free cancer cells can spread all over the whole body with blood or lymph fluid, causing metastasis and endangering life. At present, breast cancer has become a common tumor that threatens women's physical and mental health.

The worldwide incidence of breast cancer has been increasing since the end of 1970s. In the United States, one in eight women will have breast cancer in lifetime. China is not a country with high incidence of breast cancer, but it should not be optimistic. In recent years, the growth rate of breast cancer incidence in China is 1 to 2 percentage higher than that in high incidence countries.

Chimeric antigen receptor (abbreviated CAR) modified immune cells is to use genetic engineering methods to modify immune cells, which makes the immune cells express exogenous anti-tumor gene. The CAR gene mainly includes an extracellular recognition domain and an intracellular signal transduction domain: wherein the former is used to recognize tumor surface specific molecules, and the latter is used to initiate immune cell responses after the recognise of the tumor surface molecules and exert cytotoxicity. The CAR mainly uses T-cell as a carrier. However, in treatment of tumors with CAR-T cells, the levels of IL-6 and other cytokines will increase dramatically, resulting in cytokine release syndrome phenomenon and problems such as on-targete/off-target toxicity and neurotoxicity, which will endanger the life of a patient in severe cases. Moreover, T cells must be isolated out of the body (this process is time-consuming and expensive). Furthermore, considering the T cells are modified for specific patients, however some patients may not be competent for collection of T cells or do not have enough time to wait for the preparation process of T cells. Although nowadays the CAR-T is developing towards a universal CAR-T, which also increases the clinical risk and the difficulty of operation. In addition, to face the high cost of CAR-T, these limitations may lead to that some patients who are expected to benefit from CAR-T immunotherapy cannot be administered.

Natural killer (abbreviated NK) cells are an important part of the non-specific immune system and are the key mediator cells of the innate immune system. NK cells are a kind of broad spectrum immune cells, which has the specific function of rapidly discovering and destroying abnormal cells (such as cancer cells or virus infected cells), and can demonstrate strong ability of dissolving abnormal cells without requiring being sensitized in advance or HLA matching. Using immune cells (including NK cells) to treat cancer is a new trend in recent years. This new therapy is expected to be promising for the treatment of tumors that are refractory to traditional surgery, chemotherapy and radiotherapy.

SUMMARY

In view of this, the present invention provides a nucleotide sequence for encoding CAR, a ROBO1 CAR-NK cell for expressing the CAR, and preparation and application thereof. The cell can specifically recognize and kill tumor, and has more effective tumor killing activity, and has little toxic side effect and higher safety.

The present invention provides a nucleotide sequence for encoding a chimeric antigen receptor, which comprises an antigen binding domain, a transmembrane domain and a costimulatory signal transduction region, wherein the antigen binding domain can specifically bind to tumor specific antigen ROBO1, and activate NK cells through the transmembrane domain and the costimulatory signal transduction region.

Illustratively, the antigen binding domain can specifically bind to one or more of Ig1, Ig2, Ig3, Ig4, Ig5, FN1, FN2 and FN3 domain of tumor specific antigen ROBO1.

Illustratively, the antigen binding domain can specifically bind to the FN3 domain of the tumor specific antigen ROBO1.

Illustratively, the antigen binding domain is an antibody or an antigen binding fragment thereof specifically binding to the FN3 domain of ROBO1, and the antigen binding fragment is Fab or ScFV.

Illustratively, the transmembrane domain is selected from one or more of CD28, CD3ε, CD45, CD4, CD5, CD8, CD9, CD16, CD22, CD33, CD37, CD134, CD137, ICOS and CD154.

Preferably, the transmembrane domain is CD8 transmembrane domain.

Illustratively, the costimulatory signal transduction region contains the intracellular domain of costimulatory molecule, which is selected from one or more of CD3ζ, CD3γ, CD3δ, CD3ε, CD5, CD22, CD79a, CD79b, CD66d, CD2, CD4, CD5, CD28, CD134, CD137, ICOS, CD154, 4-1BB and OX40.

Preferably, the costimulatory signal transduction region contains the intracellular domains of 4-1BB and CD3ζ.

In a specific embodiment of the present invention, the chimeric antigen receptor is a fusion protein with a structure of ScFV-CD8-4-1BB-CD3ζ, and the amino acids sequence of the fusion protein ScFV-CD8-4-1BB-CD3ζ is shown in SEQ ID NO: 1 or SEQ ID NO: 3.

In a specific embodiment of the invention, the encoding nucleotide sequence of the fusion proteinScFV-CD8-4-1BB-CD3ζ is shown in SEQ ID NO: 2 or SEQ ID NO: 4.

Another aspect of the present invention provides a construct, comprising the above-mentioned nucleotide sequence for encoding a chimeric antigen receptor.

Another aspect of the present invention provides a chimeric antigen receptor encoded by the above-mentioned nucleotide sequence.

Another aspect of the present invention provides a ROBO1 CAR-NK cell, which can express a chimeric antigen receptor, wherein the chimeric antigen receptor comprises an antigen binding domain, a transmembrane domain and a costimulatory signal transduction region, and the antigen binding domain can specifically bind to tumor specific antigen ROBO1 and can activate NK cells through the transmembrane domain and the costimulatory signal transduction region.

Illustratively, the antigen binding domain can specifically bind to one or more of Ig1, Ig2, Ig3, Ig4, Ig5, FN1, FN2 and FN3 domain of tumor specific antigen ROBO1.

Illustratively, the antigen binding domain can specifically bind to the FN3 domain of the tumor specific antigen ROBO1.

Illustratively, the antigen binding domain is an antibody or an antigen binding fragment thereof specifically binding to the FN3 domain of ROBO1, wherein the antigen binding fragment is Fab or ScFV.

Illustratively, the transmembrane domain is selected from one or more of CD28, CD3ε, CD45, CD4, CD5, CD8, CD9, CD16, CD22, CD33, CD37, CD134, CD137, ICOS and CD154; preferably, the transmembrane domain is CD8 transmembrane domain; and/or the costimulatory signal transduction region contains the intracellular domain of costimulatory molecule, which is selected from one or more of CD3ζ, CD3γ, CD3δ, CD3ε, CD5, CD22, CD79a, CD79b, CD66d, CD2, CD4, CD5, CD28, CD134, CD137, ICOS, CD154, 4-1BB and OX40; preferably, the costimulatory signal transduction region contains the intracellular domains of 4-1BB and CD3ζ.

Illustratively, the ROBO1 CAR-NK cell can express fusion protein ScFV-CD8-4-1BB-CD3ζ, which can specifically recognize ROBO1 molecules and target the ROBO1-FN3 domain.

In a specific embodiment of the present invention, the amino acids sequence of the fusion proteinScFV-CD8-4-1BB-CD3ζ is shown in SEQ ID NO: 1 or SEQ ID NO: 3 or homologous sequences thereof.

Illustratively, the nucleotide sequences of the fusion protein ScFV-CD8-4-1BB-CD3ζ is shown in SEQ ID NO: 2 or SEQ ID NO: 4 or homologous sequences thereof.

In a specific embodiment of the invention, the ROBO1 CAR-NK cell can effectively destroy or kill lung cancer cell line, pancreatic cancer cell line, hepatoma cell line, glioma cell line, breast cancer cell line, colon cancer cell line or prostate cancer cell line.

Illustratively, the cell lung cancer cell line is H1299 or A549.

Illustratively, the pancreatic cancer cell line is ASPC-1 or BXPC3.

Illustratively, the hepatoma cell line is HepG2.

Illustratively, the glioma cell line is U87-MG or SH-SY5Y.

Illustratively, the breast cancer cell line is MCF-7, HCC1143, HCC1187, HCC1599, HCC1806, HCC38, HCC1937 or MDA-MB-453.

Another aspect of the present invention provides a preparation method of the above-mentioned ROBO1 CAR-NK cells, which includes the following steps:

(1) synthesizing and amplifying the nucleotide sequence, and cloning the nucleotide sequence into a lentiviral expression vector; preferably, the nucleotide sequence is the gene of fusion protein ScFV-CD8-4-1BB-CD3ζ;

(2) infecting 293T cells with a lentiviral packaging plasmid and the lentiviral expression vector plasmid prepared by step (1), packaging and preparing a lentivirus;

(3) infecting NK-92 cells with the lentivirus prepared in step (2) to obtain CAR-NK cells. The present invention also provides a pharmaceutical composition comprising the above-mentioned ROBO1 CAR-NK cells.

Illustratively, the effector-to-target ratio of ROBO1 CAR-NK cells to tumor cells in the pharmaceutical composition is 0.5:2 to 1:2; preferably, the effector-to-target ratio is 0.5:1 to 1:1.

Illustratively, the pharmaceutical composition also includes optional pharmaceutically acceptable adjuvants.

Illustratively, the dosage form of the pharmaceutical composition is aqua.

The pharmaceutically acceptable adjuvants described herein are preferably pharmaceutically acceptable adjuvants for injection, such as isotonic sterile salt solutions (such as sodium dihydrogen phosphate, sodium hydrogen phosphate, sodium chloride, potassium chloride, calcium chloride, magnesium chloride, and the like, or the mixtures thereof), or dried, such as freeze-dried compositions, which are properly formed into injectable solvent with sterile water or normal saline.

The present invention also provides a method for treating and/or preventing cancer by using the above-mentioned ROBO1 CAR-NK cells or the pharmaceutical composition, including administering an effective amount of drug containing ROBO1 CAR-NK cells to patients needing treatment.

Illustratively, the cancer is a tumor with highly expressing of ROBO1 molecules and related diseases.

Illustratively, the cancer is liver cancer, breast cancer, colon cancer, pancreatic cancer, prostate cancer, glioma, or lung cancer.

In a specific embodiment of the present invention, the cancer is breast cancer.

Illustratively, the dosage of ROBO1 CAR-NK cells is $0.5\times10^9$ cells/time to $5\times10^9$ cells/time.

Illustratively, the administration mode of the drugs containing ROBO1 CAR-NK cells is intratumoral injection, intravenous injection, intrathoracic injection or local intervention.

In a specific embodiment of the present invention, the administration mode of the drugs containing ROBO1 CAR-NK cells is intravenous injection.

The present invention also provides a use of the above-mentioned ROBO1 CAR-NK cells or the pharmaceutical composition in the preparation of medicaments for treating and/or preventing cancer.

Illustratively, the cancer is a tumor with highly expressing of ROBO1 molecules and related diseases.

Illustratively, the cancer is liver cancer, breast cancer, colon cancer, pancreatic cancer, prostate cancer, glioma, or lung cancer; preferably, the cancer is breast cancer.

The ROBO1 CAR-NK cells provided by the present invention has at least one of the following advantages: it can specifically kill tumor cells by using ROBO1 CAR-NK cells through using ROBO1 antibody for the construction of CAR-NK cells and using ROBO1 molecules as target antigens; it can be used as a therapeutic agent for tumor diseases, for the treatment of tumor with highly expressing ROBO1, without harmful phenomena such as cytokine release syndrome, thus providing a new treatment for the tumors which are refractory to traditional surgery, chemotherapy and radiotherapy; it can improve its targeting ability by transforming NK92 cells with CAR, moreover, greatly improve its anti-tumor ability while increasing anti-tumor targeting sites ROBO1; in addition, the ROBO1 CAR-NK cells has a significantly better specific lysis activity compared with ROBO1 CAR-T cells, and can be more effective in killing tumors; that is to say, by transforming NK92 cells with CAR, the ROBO1 CAR-NK cells constructed by the present invention can not only have significantly improved targeting ability, but also get higher safety, lower toxicity and side effects and lower costs by transforming NK cells; and because of the synergistic effect of NK cells, CAR and anti-tumor target sites ROBO1, the specific lysis activity is significant and obviously better than ROBO1 CAR-T cells.

DETAILED DESCRIPTION OF THE EMBODIMENTS

Figure 1:
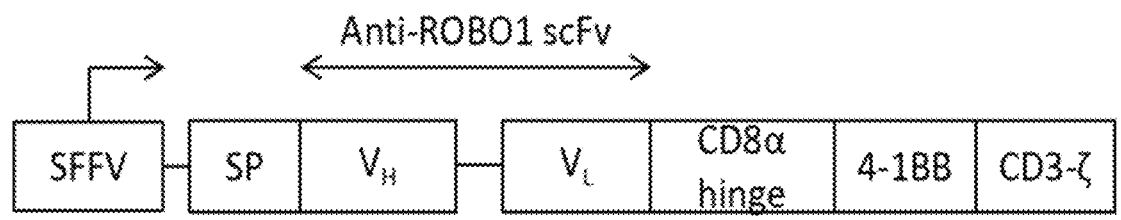
FIG. 1 shows the schematic construction map of the lentiviral vector PRRLSIN-ScFV (anti ROBO1-FN3) provided in Example 1.

Unless otherwise defined, all technical and scientific terms used in the present invention have the same meaning as those generally understood by a person of ordinary skilled in the art.

Specifically, the nucleotide sequence for encoding fusion protein ScFV-CD8-4-1BB-CD3ζ in the present invention is any DNA sequence that can encode the fusion protein; preferably, the sequence is SEQ ID NO: 2 or its complementary sequence, or SEQ ID NO: 4 or its complementary sequence. On the other hand, the nucleotide sequence for encoding fusion protein ScFV-CD8-4-1BB-CD3ζ in the present invention can be the polynucleotide or its complementary sequence which can hybridize with the nucleotide sequence of SEQ ID NO:2 or SEQ ID NO:4 under stringent condition, and can encode the fusion protein.

The term of "stringent condition" described in this paper can be selected from low stringent condition, moderate stringent condition and high stringent condition. Illustratively, "low stringent condition" can be the conditions of 30° C., 5×SSC, 5×Denhardt solution, 0.5% SDS and 52% formamide; "moderate stringent condition" can be the conditions of 40° C., 5×SSC, 5×Denhardt solution, 0.5% SDS and 52% formamide; "high stringent condition" can be the condition of 50° C., 5×SSC, 5×Denhardt solution, 0.5% SDS and 52% formamide. The skilled in the art should understand that the higher the temperature is, the more highly homologous polynucleotides can be obtained. Besides, the skilled in the art can choose the factors which can affect the stringency of hybridization, such as temperature, probe concentration, probe length, ionic strength, time and salt concentration, to achieve the corresponding stringency.

Besides, the hybridizable polynucleotides can also be the polynucleotides which has the identity of about 60% or more, 70% or more, 71% or more, 72% or more, 73% or more, 74% or more, 75% or more, 76% or more, 77% or above, 78% or above, 79% or above, 80% or above, 81% or above, 82% or above, 83% or above, 84% or above, 85% or above, 86% or above, 87% or above, 88% or above, 89% or above, 90% or more, 91% or more, 92% or above, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more to polynucleotide encoding sequence number 6 when calculated using default parameters set by the homologous search softwares such as FASTA or BLAST or the like.

The identity of nucleotide sequences can be determined by using algorithm rule BLAST of Karlin and Altschul (Proc. Natl. Acad. Sci. USA 87: 2264-2268, 1990; Proc. Natl. Acad. Sci. USA 90:5873, 1993). The softwares of BLASTN and BLASTX based on the algorithm rule BLAST have been developed (Altschul S F, et al: J Mol Biol 215: 403, 1990). When analyzing the base sequence using BLASTX, the parameters can be exemplarily set as score=100 and word length=12; besides, when analyzing the amino acid sequence using BLASTX, the parameters can be exemplarily set as score=50 and word length=3; when using softwares of BLAST and Gapped BLAST, parameters can be set as default.

The effective dose of the drug in the present invention can be any amount, as long as it would be effective to treat cancer or alleviate cancer symptoms or inhibit cancer cells, exemplarily it can be equivalent to about $0.1 \times 10^9$ cells to $10.0 \times 10^9$ cells. The determination of effective dose is within the ability of the skilled in the art, especially considering the inspiration of the content disclosed in this present invention.

According to the present invention, the pharmaceutical products (drugs, pharmaceuticals) or pharmaceutical compositions of the present invention can be administered to the subjects at any effective dose. Preferably, the pharmaceutical products (drugs, pharmaceuticals) or pharmaceutical compositions of the present invention can be administered at multiple doses, for example, from about 2 to about 20 doses, preferably from about 4 to about 10 doses. In a specific preferred embodiment, the pharmaceutical products (drugs, pharmaceuticals) or pharmaceutical compositions of the present invention is administered to a subject at the frequency of about once every three weeks via injection, infusion or oral administration, among the others. In a particular preferred embodiment, the drug is administered with intra-tumor injection.

It should be understood that the pharmaceutical products (drugs, pharmaceuticals) or pharmaceutical compositions of the present invention can be formulated in any suitable way for administering drugs.

The dosage unit of the pharmaceutical product (drug, pharmaceutical) or pharmaceutical composition of the present invention is based on the administration mode of the drug. For example, the dosage unit can be suitable for dosing frequency, such as more than once a day, once a week, once a month, etc. The dosage unit can be on the basis of two times per week, that is, two times a week, such as once every three days.

The instructions contained in the pharmaceutical product of the present invention can contain the following content: indications (such as breast cancer), dosage (such as the above illustrative description), and possible side effects and so on.

In the present invention, the term "antibody" refers to the immunoglobulin molecule specifically binding to antigen. The antibody can be a complete immunoglobulin originated from natural sources or from a recombination source, and can be an immuno reactive part of a whole immunoglobulin. The antibody is usually a tetramer of immunoglobulin molecules. Antibodies in the present invention can exist in various forms, including, for example, polyclonal antibody, monoclonal antibody, Fv, Fab and F(ab)2, as well as single chain antibody and humanized antibody (Harlowet., 1999, In: Using Antibodies: A Laboratory Manual, Cold Spring Harbor Laboratory Press, NY; Harlow et., 1989, In: Antibodies: A Laboratory Manual, Cold Spring Harbor, N.Y.; Houston et., 1988, Proc. Natl. Acad. Sci. USA 85:5879-5883; Bird et., 1988, Science 242: 423-426) and the like.

The term "antibody fragment" refers to a part of the whole antibody, and refers to the antigenic determining variable region of the whole antibody. Examples of the antibody fragments include, but are not limited to, Fab, Fab', F(ab')2 and Fv fragments. Optionally, antibody fragments can form into linear antibody, ScFV antibody and multiple specific antibody.

Unless otherwise specified, "encoding nucleotide" includes all nucleotide sequences that are degenerate versions of each other and can encode the same amino acid sequence. The nucleotide sequence for encoding protein can contain introns.

The term "lentivirus" refers to the genus of retroviruses, which can effectively infect non-cyclical and mitotic cells. They can transmit significant amounts of genetic information into DNA of host cells, so that they are one of the most effective methods of gene delivery vectors.

The term "promoter" is defined as a DNA sequence needed to start the specific transcription of polynucleotide sequences, which is identified by organelle or is to guide organelle.

The term "specific binding" means recognizing specific antigens but basically not recognizing or binding other molecules in the sample.

The term "carrier" or "vector" is a physical composition, which includes isolated nucleic acids, and can be used to transfer isolated nucleic acids into a cell. Many vectors which have been known in this field, including, but not limited to, linear polynucleotides, and the polynucleotides, plasmids and viruses related to ions or amphiphilic compound. The term "carrier" or "vector" includes autonomously replicating plasmids or viruses. The term should also be interpreted as including non-plasmid or non-viral compounds that facilitate transferring nucleic acids into cells, such as polylysine compounds and liposomes and the like. Examples of viral vectors include, but are not limited to, adenovirus vectors, adeno-associated virus vectors, retroviral vectors, and so on.

The term "cancer" is defined as a disease characterized by rapid and uncontrolled growth of aberrant cells. Cancer cells can spread locally or spread to other parts of the body through blood flow and lymphatic system. Examples of various cancers include, but are not limited to, breast cancer, prostate cancer, ovarian cancer, cervical cancer, skin cancer, pancreatic cancer, colorectal cancer, kidney cancer, liver cancer, brain cancer, lymphoma, and leucocythemia, lung cancer and so on.

As used in this text, "include", "contain", "comprise" or "characterized in" are synonymous, and are inclusive or open, and do not exclude other elements or methods or steps that are not stated. Any expression of the term "include" in this paper, especially when describing the methods, uses or products of the present invention, should be understood as including those products, methods and uses which are basically or totally composed of the components or elements or steps. The illustrative description in the present invention can be practiced properly without any one or more components or one or more restrictions which are not specifically described in this paper.

The terms and expressions used in this paper are used as descriptive rather than restrictive terms, and it is not expected to exclude any equivalents of the illustrated or described characteristics or their parts in the use of such terms and expressions, but it should be recognized that various modifications are acceptable within the scope of the present invention. Therefore, it should be understood that although the present invention has been specifically disclosed through preferred embodiments and optional features, the skilled in the art can adopt the modifications and variations of the concepts disclosed in this paper, and such modifications and variations are regarded as within the scope defined by the additional claims of the present invention.

The English names in this paper are not case sensitive, for example, the terms of ROBO1, Robo1, robo1 and the like share the same meaning; the terms of Robo1 CAR-NK and Robo1-CAR NK share the same meaning; the terms of anti Robo1 CAR-NK and Anti Robo1-CAR NK share the same meaning as CAR-NK cell of anti ROBO1 molecule; the terms of anti Robo1M CAR-NK and Anti Robo1M-CAR NK share the same meaning as mutant CAR-NK cell of anti ROBO1 molecule; the terms of NK-92 and NK92 share the same meaning as NK92 cells.

The term of "NK" described in the present invention is a human normal NK cell or NKT cell, or NK cell line including NK-92 cell, YT cell, NKL cell, HANK-1 cell, NK-YS cell, KHYG-1 cell, SNK-6 cell and IMC-1 cell. In the specific embodiment of the invention, NK-92 cell is taken as an example.

For a clearer explanation of the invention, it is further explained in detail in combination with the following embodiments. But these embodiments are merely exemplary descriptions of the invention and not intended to limit the present invention.

Example 1 Preparation of Lentiviral Vector

The sequences of ScFV(Anti ROBO1-FN3)-CD8-4-1BB-CD3ζ fusion gene (its amino acid sequence is shown in SEQ ID NO:1 and its gene sequence is shown in SEQ ID NO:2) and the sequences of mutant ScFV(Anti ROBO1-FN3)-CD8-4-1BB-CD3ζ fusion gene (its amino acid sequence is shown in SEQ ID NO:3 and its gene sequence is shown in SEQ ID NO:4) synthesized separately. The ScFV(Anti ROBO1-FN3)-CD8-4-1BB-CD3ζ fusion gene is taken as an example to illustrate the preparation process of ROBO1 CAR-NK cells, while the preparation process of ROBO1M CAR-NK cells using mutant ScFV(Anti ROBO1-FN3)-CD8-4-1BB-CD3ζ fusion gene is identical.

The sequence of ScFV(Anti ROBO1-FN3)-CD8-4-1BB-CD3ζ fusion gene was transformed and ligated into PRRS-LIN vector by enzyme digestion, wherein the upstream of the gene was EP-la promoter. The vector was transformed into Stb13 *Escherichia coli* strain, which was screened by ampicillin to obtain positive clones. Then plasmid was extracted and the clone was identified by enzyme digestion, so that PRRLSIN-ScFV(anti ROBO1-FN3) lentiviral vector was obtained (as shown in FIG. 1).

Example 2 Preparation of Lentivirus (1) 24 hours before transfection, 293T cells were inoculated into 15 cm petri dishes at about $8 \times 10^6$ per dish. Ensure that the convergence degree of 293T cells was about 80% and the 293T cells were evenly distributed in petri dishes during the transfection.

(2) Preparation of solution A and solution B

Solution A: 6.25 mL of 2×HEPES buffered solution (the effect is better when the quantity is a package of 5 dishes together)

Solution B was a mixture by adding the following plasmids respectively: 112.5 μg PRRLSIN-ScFV(anti ROBO1-FN3) (target plasmid); 39.5 μg pMD2.G(VSV-G envelop); 73 μg pCMVR8.74 (gag,pol,tat,rev); 625 μl 2M calcium ion solution. The total volume of solution B was 6.25 mL.

Solution B was mixed completely, and dropwise added into solution A while gently swirling solution A, so that a mixture of solution A and B was obtained, which was then rested to stand for 5 to 15 minutes. The mixture of solution A and B was gently swirled and dropwise added into a petri dish containing 293T cells. The obtained petri dish was gently shaken back and forth to evenly distribute the mixture of DNA and calcium ions. Then the petri dish was incubated for 16-18 hours in incubator (without being rotated). The medium was replaced by fresh one and the cultivation was continued. The supernatants containing virus was collected after 48 hours and 72 hours separately, and the supernatants was centrifuged at 500 g for 10 min at 25° C. and then filtered by PES membrane (0.45 μm). Ultra-clear SW28 centrifuge tubes (by the manufacture of BECKMAN COULTER) were sterilized with 70% ethanol and then disinfected under ultraviolet light for 30 min. The filtered lentivirus supernatants were transferred into the prepared centrifuge tube which had been carefully laid a layer of 20% sucrose (1 mL sucrose per 8 mL supernatant) at the bottom. The liquid was balanced with PBS buffer and then centrifuged at 25000 rpm (82,700 g) at 4° C. for 2 hours. The centrifuge tubes were taken out carefully, and the supernatants were poured out, and then centrifuge tubes were inverted to remove the residual liquid. Then the centrifuge tubes were added by 100 μl PBS, sealed, stood at 4° C. for 2 hours, swirled every 20 minutes, and finally centrifuged (500 g) for 1 min (25° C.) to collect the supernatant containing virus. The collected supernatant was cooled on ice and then stored at −80° C.

Example 3 Preparation of ROBO1 CAR-NK Cells

The density of NK-92 cells was adjusted to $2 \times 10^5$/mL to $3 \times 10^5$/mL. The virus obtained from Example 2 was added to NK-92 cells according to the volume ratio (V/V) of virus: cell culture medium=1:5, while 8 μg/mL polyamine was added at the same time. 4 hours later, equivalent amount of fresh complete medium was added to adjust the cell density to $1 \times 10^5$/mL for further cultivation. The next day, all cells were centrifuged and added by fresh medium for further cultivation. Fresh medium was added every 1 to 2 days to maintain cell density at $2 \times 10^5$/mL to $3 \times 10^5$/mL. CAR antibody staining was performed after 72 hours, and ROBO1 CAR NK-92 positive cells sorted by flow cytometry for culture expansion. The color change, cell density and cell morphology of the medium were observed daily and recorded accordingly.

After the flow cytometry, positive ROBO1 CAR NK-92 cells were continuously cultured in GMP workshop, and then expanded to the required measurement for clinical use. After that, centrifugation and three washing (by PBS solution) were performed, then the obtained ROBO1 CAR-NK 92 cells were resuspended in normal saline for clinical reinfusion.

Before clinical reinfusion, the quality of ROBO1 CAR-NK 92 was tested by reference Pharmacopoeia to guarantee the safety of cells. The results of the test are shown in Table 1.

TABLE 1 quality detection of ROBO1 CAR-NK 92 cells

| Release parameters | GMP release criteria | Actual test results |
|---|---|---|
| Sterility test (liquid cultivation) | negative | negative |
| Sterility test (Gram staining) | negative | negative |
| Cell viability (trypan blue staining) | >95% | 98% |
| Endotoxin (limulus reagent) | <5 EU/kg/hr | <5 EU/kg/hr |
| CAR positive rate(Flow detection) | >90% | 96.31% (shown in FIG. 2) |
| Mycoplasma DNA (PCR method) | negative | negative |
| CD56+ (Flow detection) | positive | positive (shown in FIG. 3) |

Figure 2A:
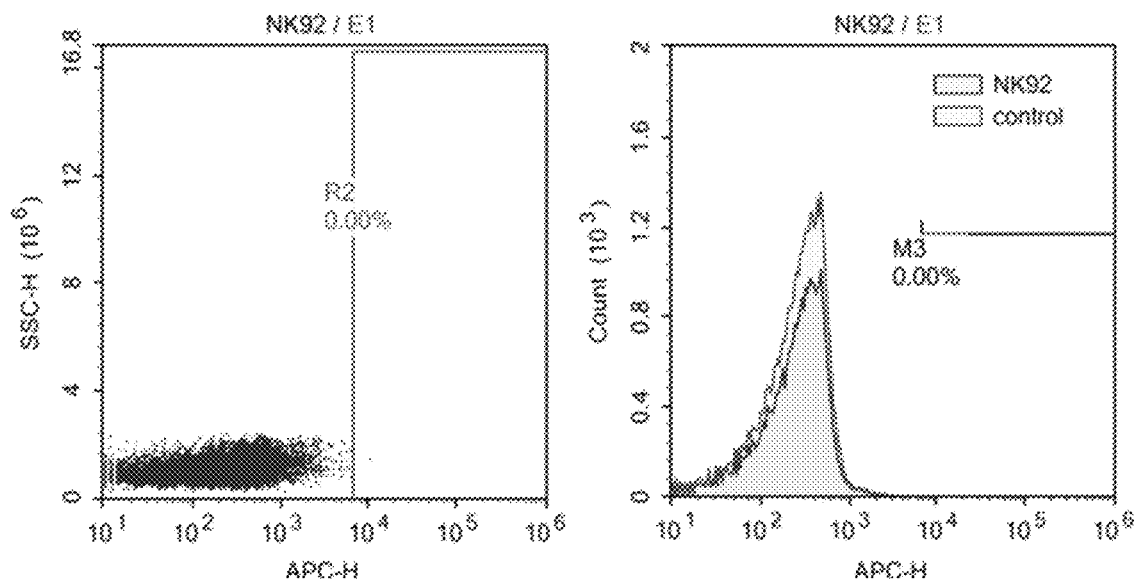
FIGS. 2a to 2b shows a result of positive rate of CAR cells of ROBO1 CAR-NK detected by flow cytometry provided in Example 3.
Figure 2B:
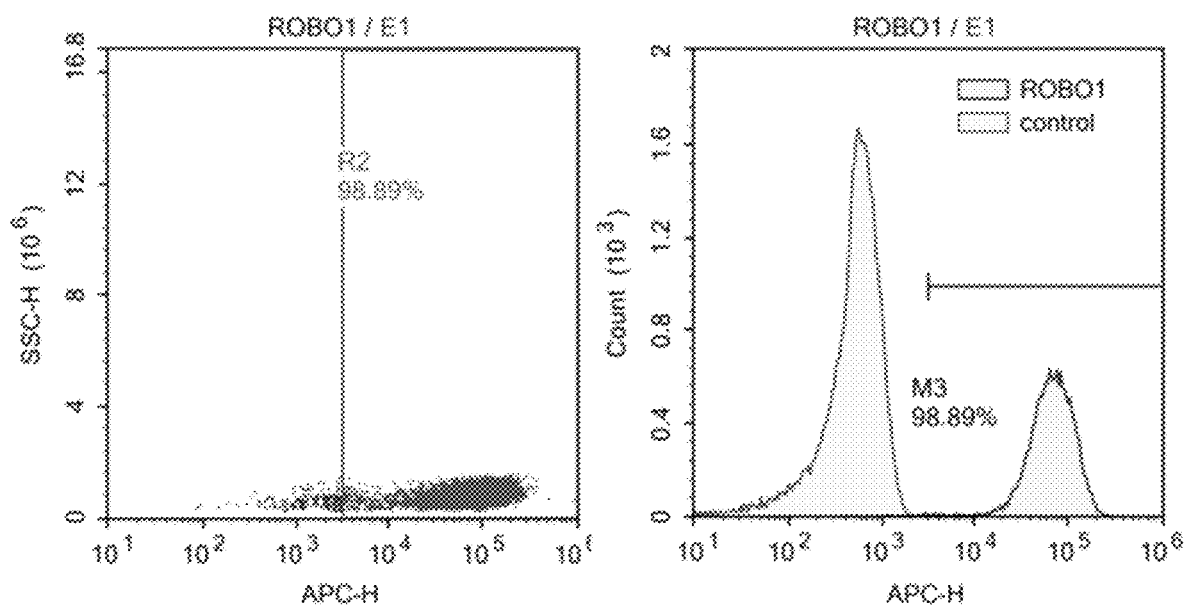

The positive rate of CAR NK-92 cells was detected by flow cytometry, and the results were shown in FIG. 2a and FIG. 2b. In FIG. 2a and FIG. 2b, the antibodies used were shown as APC fluorescence label and represented on the abscissa. If NK92 cells successfully expressed CAR molecules, the signal value would increase significantly. It can be seen from FIG. 2a and FIG. 2b that the signal value of the fluorescence label increased significantly, indicating that CAR molecules were successfully expressed by NK92 cells. The positive rate of CAR-NK92 was 98.89%.

Figure 3A:
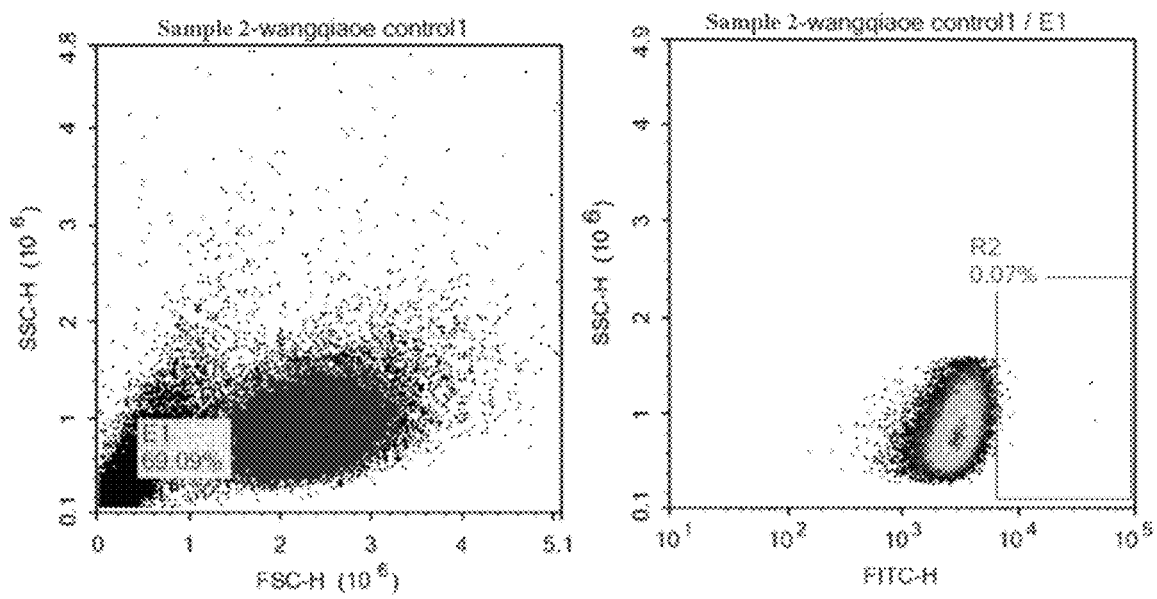
FIGS. 3a to 3b shows a result of positive rate of CD56 molecules of ROBO1 CAR-NK detected by flow cytometry provided in Example 3.
Figure 3B:
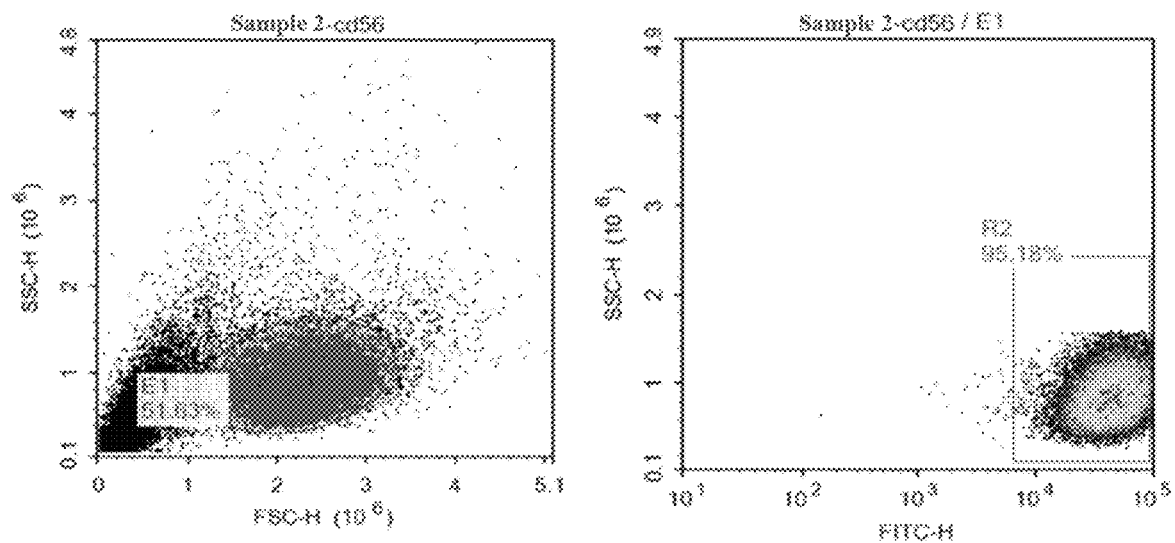

FIGS. 3a and 3b show the results of the positive rate of CD56 molecules detected by ROBO1 CAR-NK flow detection. FIG. 3a is the control group, and FIG. 3b is the experimental group. It can be seen from FIGS. 3a and 3b that the CD56 molecule is positive indicating that the prepared CAR-NK92 cells did not lose CD56 molecules, and there was no other forms of differentiation, which means the basic characteristics of NK cells had been preserved.

ROBO1M CAR-NK cells were prepared in the same way.

Example 4 Preparation of ROBO1 CAR-T Cells (1) Preparation of T cells: 100 mL of healthy human blood was extracted and gradiently centrifuged with Ficall reagent (15/50 ml BD tube) to obtain PBMC. The isolated PBMC was active and cultivated using T cell culture medium (X-VIVO 15; serum (5%)/plasma; IL-2 300 IU (import)/ml 500 IU (domestic)/mL, penicillin-streptomycin solution 10%) to obtain the activated PBMC. The activated PBMC was resuspended, and separated T cells expressing CD3+ (usually 50% to 60% of PBMC). The ratio of magnetic beads to T cells was 3:1. T cells expressing CD3+ were collected to obtain T cells (the remaining cells can be used for other experiments).

(2) Preparation of ROBO1 CAR-T cells: T cells obtained from step (1) were cultured at density of $1\times10^6$/mL for 24 h to 48 h, and 2 to 3 days later, the medium was changed to obtain the cultured T cells. Then the cultured T cells were concentrated with fresh medium until the density of cells was $3\times10^6$/mL to $5\times10^6$/mL in order to perform the virus transduction. Then virus (prepared according to Example 2) was added according to the volume ratio (V/V) of virus: medium of =1:10, and mixed well, and then incubated at 37° C. and 5% $CO_2$ for 4 hours. After that, density of cells was diluted to $1\times10^5$/mL by adding medium. The next day, the change of medium, the centrifugation of all cells and the addition of fresh medium were performed in sequence to continue the cultivation and observation. After 2 to 3 days, the medium was changed in half (That is, half of the medium was centrifuged and diluted by fresh medium, and finally added back to culture bottles) to maintain the cell density at $2\times10^5$/mL to $3\times10^5$/mL. ROBO1 CAR-T cells were obtained after 7 days of continuous cultivation, in which the sequence of ROBO1 is the same as it of ROBO1M.

Figure 4A:
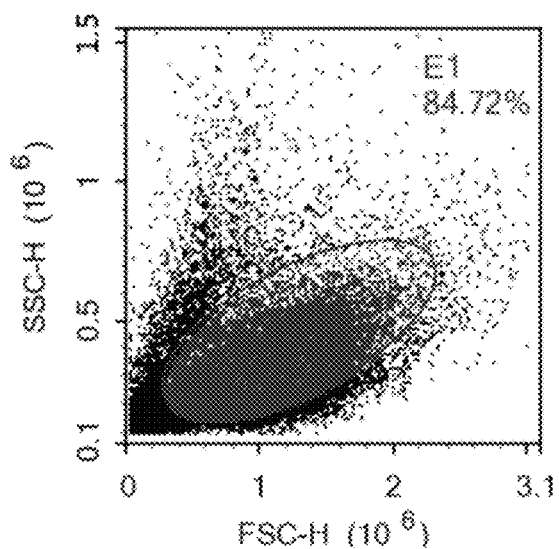
FIGS. 4a to 4b shows a result of positive rate of CAR NK-T cells detected by flow cytometry provided in Example 4.
Figure 4A:
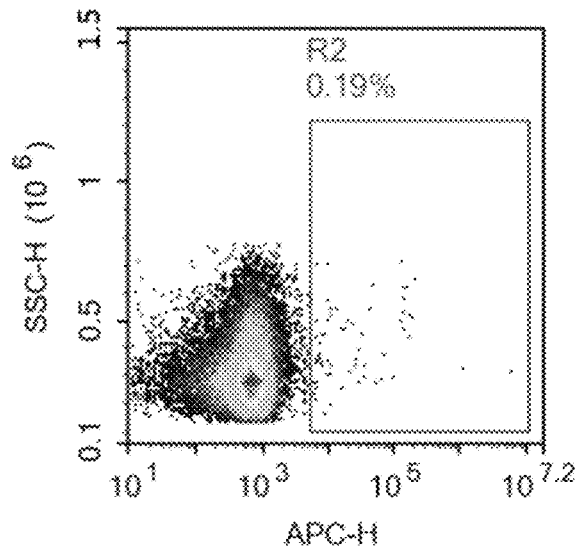
Figure 4B:
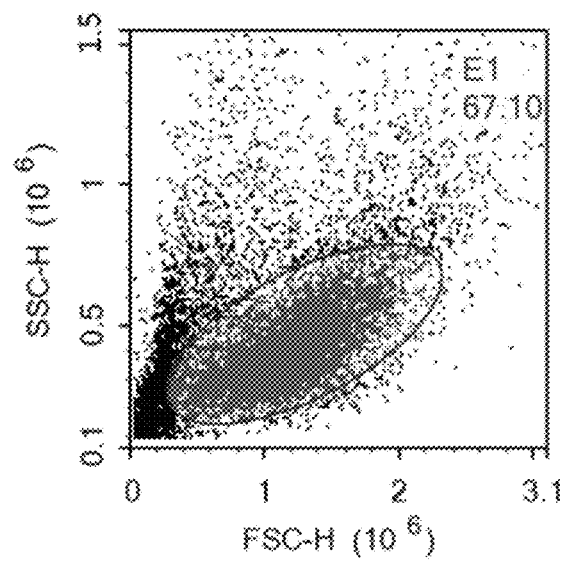
Figure 4B:
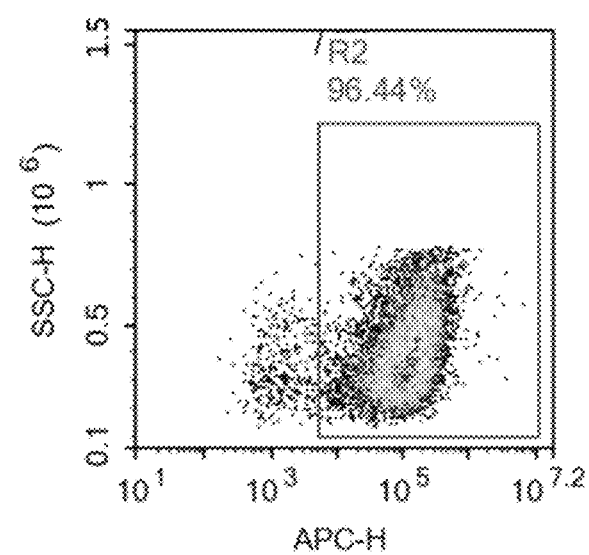

Meanwhile, ROBO1 CAR-T positive cells were sorted by flow cytometry and expanded. The positive rate of CAR NK-T cells was detected by flow cytometry and the results were shown in FIG. 4a and FIG. 4b, wherein the antibodies used were shown as APC fluorescence label and represented on the abscissa. If T cells successfully expressed CAR molecules, the signal value would increase significantly. It can be seen from FIG. 4a and FIG. 4b that the signal value of the APC fluorescence label increased significantly, indicating that CAR molecules were successfully expressed by T cells. The positive rate of T cells was 96.44%.

Example 5 Evaluation of Specific Lysis Activity of ROBO1 CAR-NK Cells and ROBO1M CAR-NK Cells on Tumor In Vitro The specific lysis activity of ROBO1 CAR-NK cells and ROBO1M CAR-NK cells on various tumor cell lines were detected using CCK-8 method (reference: Human Leukocyte Antigen-G Inhibits the Anti-Tumor Effect of Natural Killer Cells via Immunoglobulin-Like Transcript 2 in Gastric Cancer, Rui Wan Zi-Wei Wang Hui Li, et al.). The tumor cell lines include: lung cancer cell line H1299, lung cancer cell line A549, pancreatic cancer cell line ASPC-1 and hepatoma cell line HepG2. The process of the experiment includes:

(1) 1 mL of tumor cell suspension ($2\times10^4$/well) was prepared in 24-well plate and pre-incubated in incubator for 12 h.

(2) The culture supernatant of 24-well plates was discarded. 1 mL of effector cells was added to each well with the ratio of effector cells to target cells=1:1, while 1 mL of medium was added to the control well. Three parallel wells were placed in each experiment. The effector cells are incubated with target cells for 4 hours.

(3) 100 μL of CCK-8 solution was added in each well of the 24-well plate and incubated in incubator for 2 hours.

(4) The absorbance at 450 nm was measured by enzyme-labeling instrument.

(5) Specific lysis activity=(As−Ab)/(Ac−Ab)×100%;

As: test well (mixture of medium, CCK-8, CAR-NK and tumor cells);

Ac: control well (mixture of medium, CCK-8 and tumor cells);

Ab: blank control well (mixture of medium and CCK-8 without cell and CAR-NK);

The evaluation of specific lysis activity of ROBO1 CAR-NK cells and ROBO1M CAR-NK cells on tumor in vitro are shown in FIG. 5a-5d.

The experimental results in FIG. 5a-5d confirm that ROBO1-CAR NK 92 cells and ROBO1M-CAR NK 92 cells have strong specific lysis activity on all of lung cancer cell line H1299, lung cancer cell line A549, pancreatic cancer cell line ASPC-1 and hepatoma cell line HepG2, and the effect is better than that of ordinary NK-92 cells.

In addition, it can be seen from FIG. 5a-5d that the specific lysis activity of ROBO1M-CAR NK 92 cells is better than that of ROBO1-CAR NK 92 cells, and ROBO1M-CAR NK 92 cells can kill tumors more effectively. In view of this, the following clinical trials use ROBO1M-CAR NK 92 cells.

Example 6 Evaluation of Specific Lysis Acticiy of ROBO1M CAR-NK Cells on Glioma Cells The specific lysis activity of ROBO1M CAR-NK cells on glioma cell line U87-MG and glioma cell SH-SY5Y was detected by CCK-8 method. NK 92 cells were used as control. The experimental results were shown in FIG. 5F and FIG. 5E.

Figure 5A:
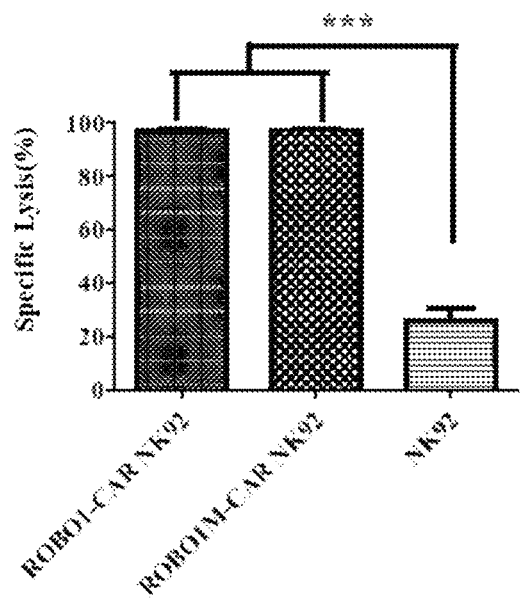
FIG. 5a shows a result of the specific lysis activity of ROBO1M-CAR NK92 cells and ROBO1M-CAR NK92 cells on H1299 cells provided in Example 5.
Figure 5B:
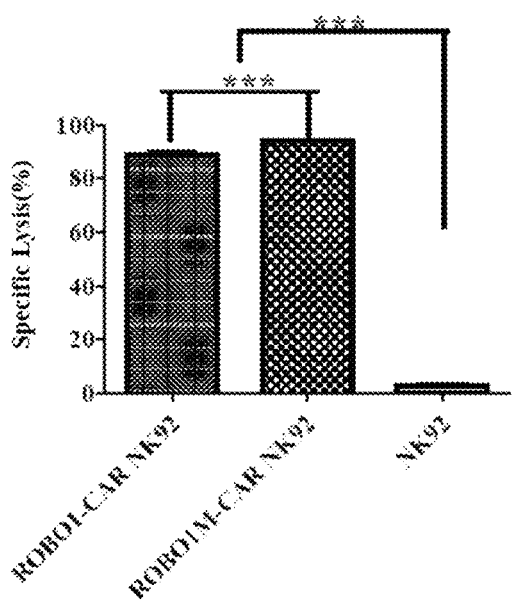
FIG. 5b shows a result of the specific lysis activity of ROBO1-CAR NK92 cells and ROBO1M-CAR NK92 cells on A549 cells provided in Example 5.
Figure 5C:
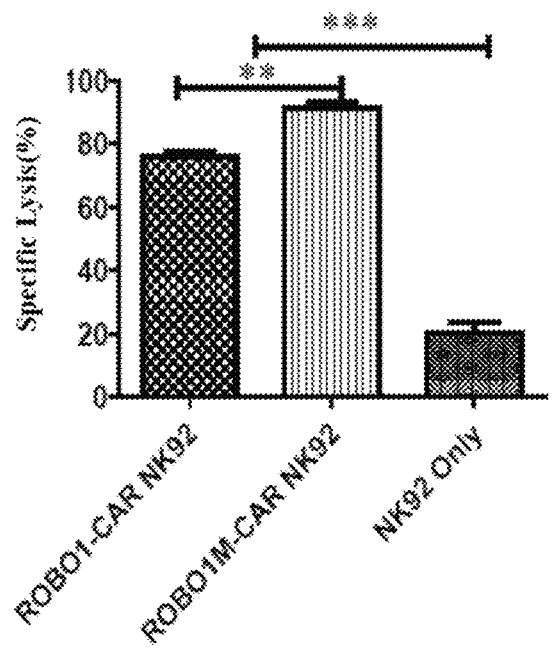
FIG. 5c shows a result of the specific lysis activity of ROBO1-CAR NK92 cells and ROBO1M-CAR NK92 cells on A549 cells provided in Example 5.
Figure 5D:
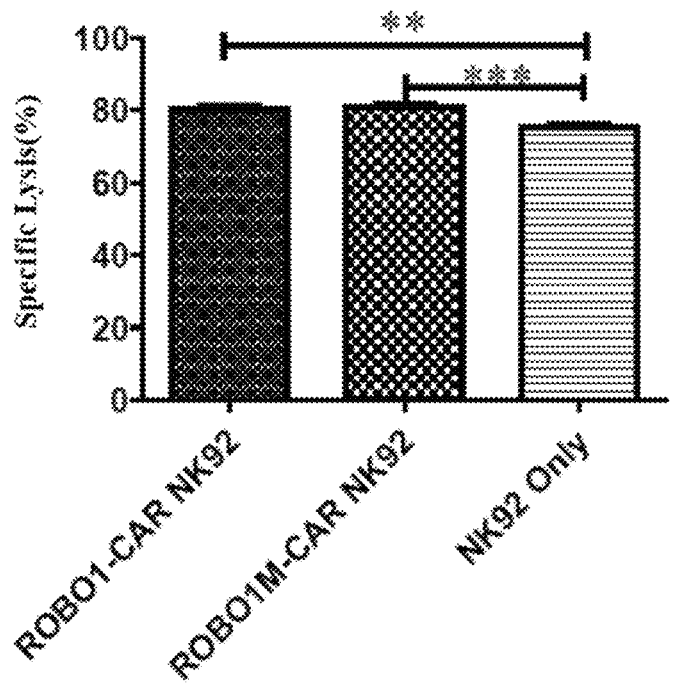
FIG. 5d shows a result of the specific lysis activity of ROBO1-CAR NK92 cells and ROBO1M-CAR NK92 cells on HepG2 cells provided in Example 5.
Figure 5E:
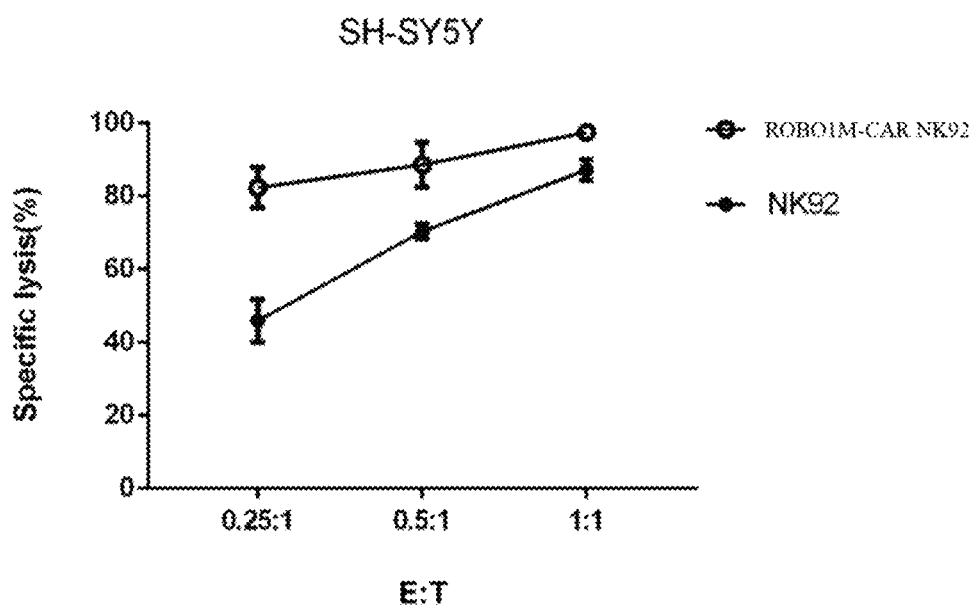
FIG. 5e shows a result of the specific lysis activity of ROBO1M-CAR NK92 cells on SH-SYSY cells provided in Example 6.
Figure 5F:
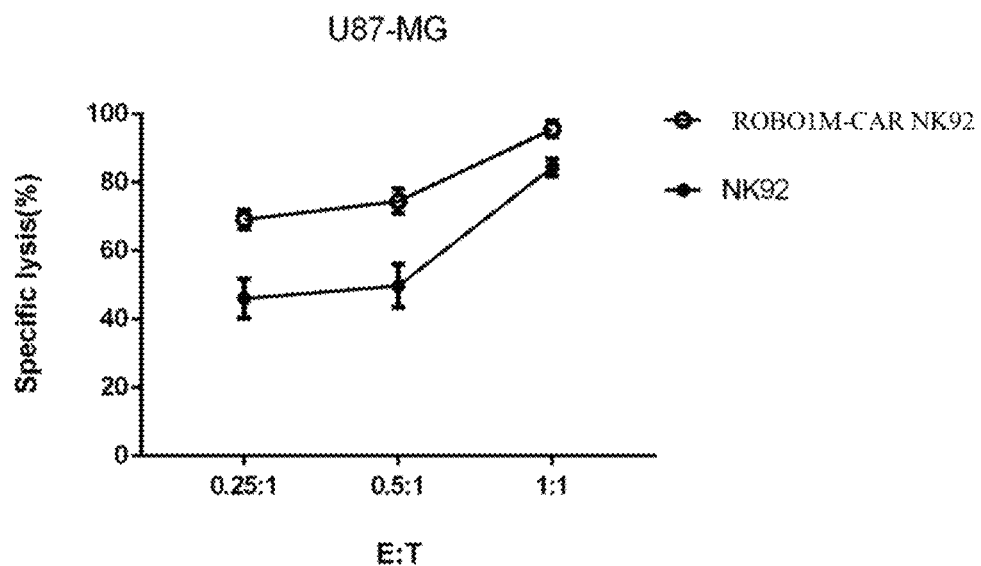
FIG. 5f shows a result of the specific lysis activity of ROBO1M-CAR NK92 cells on U87-MG cells provided in Example 6.
Figure 6A:
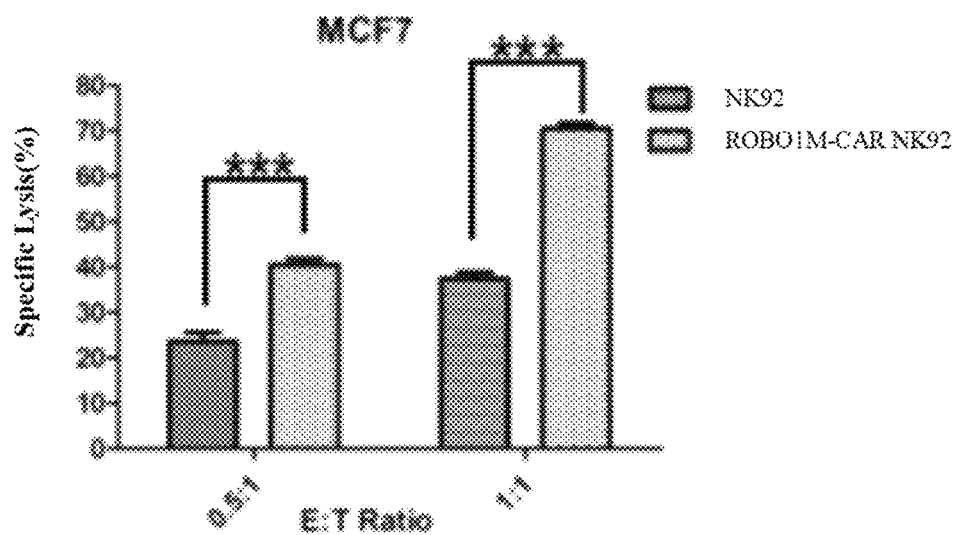
FIG. 6a shows a result of the specific lysis activity of ROBO1M-CAR NK92 cells on MCF7 cells provided in Example 7.
Figure 6B:
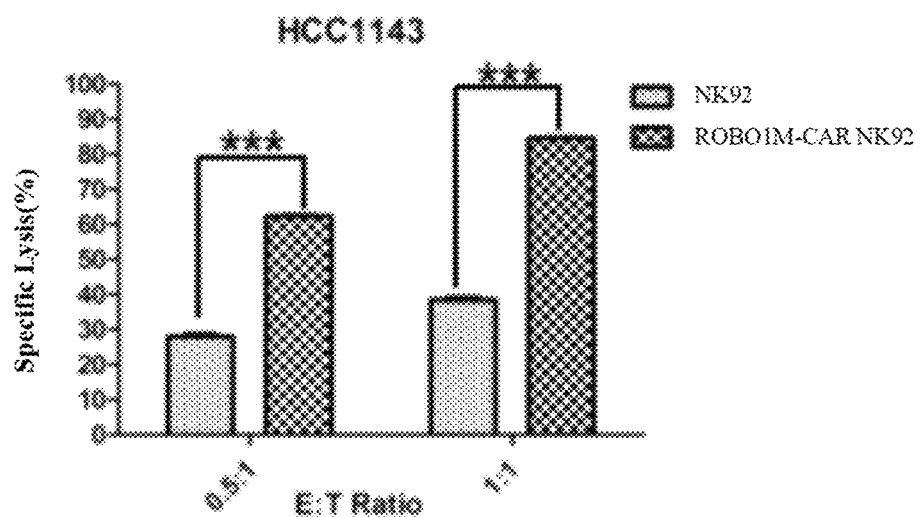
FIG. 6b shows a result of the specific lysis activity of ROBO1M-CAR NK92 cells on HCC1143 cells provided in Example 7.
Figure 6C:
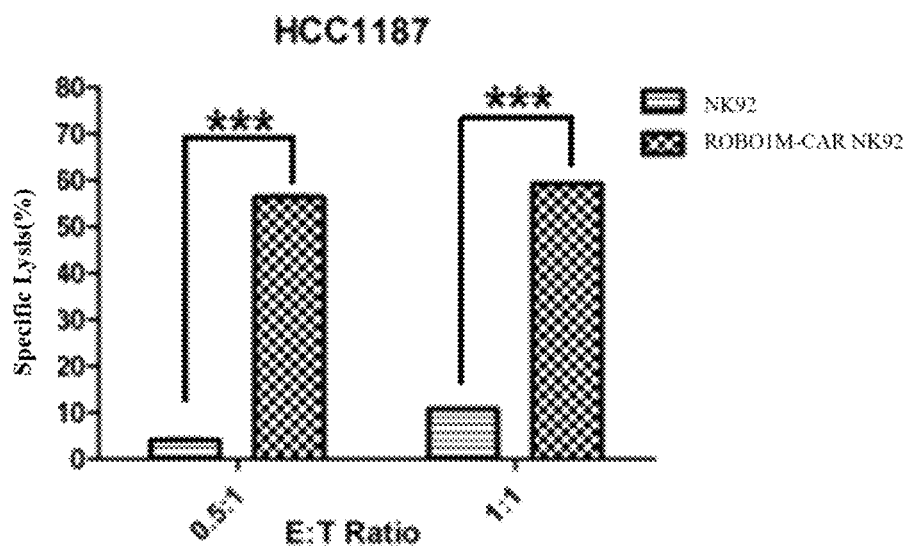
FIG. 6c shows a result of the specific lysis activity of ROBO1M-CAR NK92 cells on HCC1187 cells provided in Example 7.
Figure 6D:
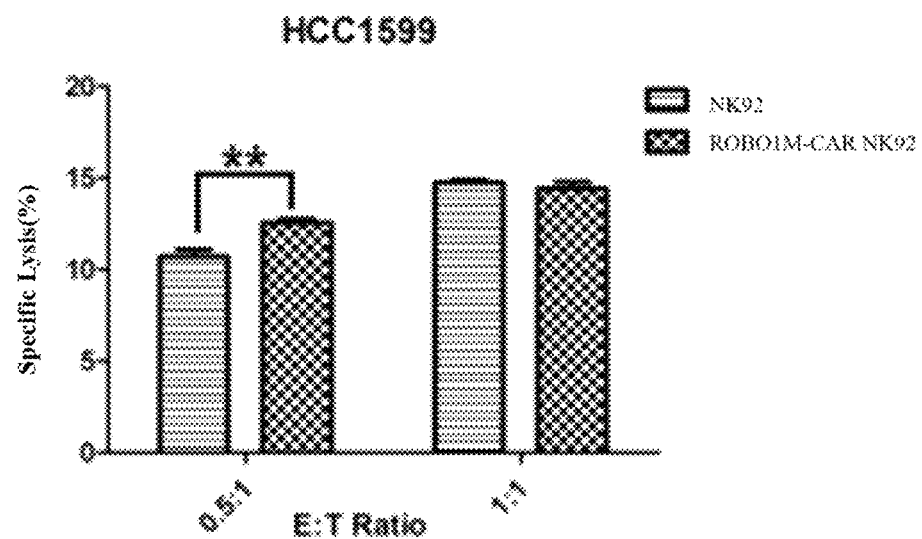
FIG. 6d shows a result of the specific lysis activity of ROBO1M-CAR NK92 cells on HCC1599 cells provided in Example 7.
Figure 6E:
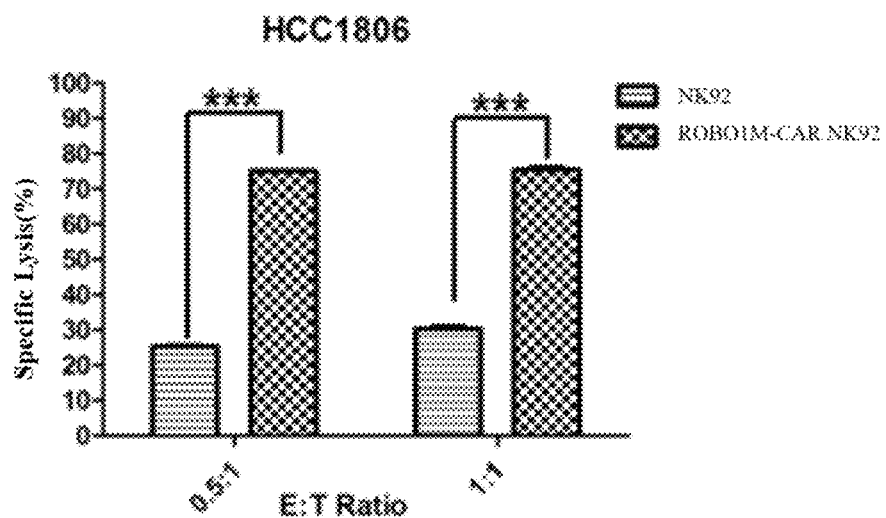
FIG. 6e shows a result of the specific lysis activity of ROBO1M-CAR NK92 cells on HCC1806 cells provided in Example 7.
Figure 6F:
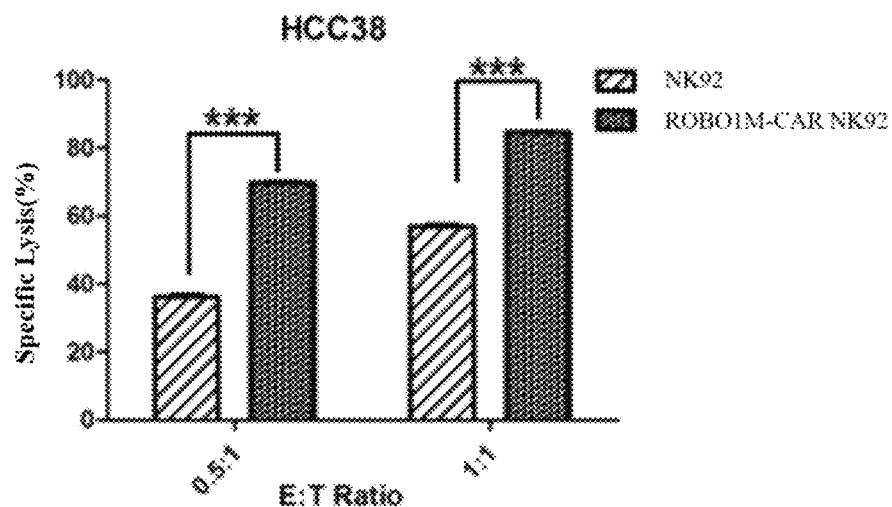
FIG. 6f shows a result of the specific lysis activity of ROBO1M-CAR NK92 cells on HCC38 cells provided in Example 7.

The experimental results in FIG. 5F and FIG. 5E show that the specific lysis activity of ROBO1M-CAR NK cells on glioma cell line U87-MG and glioma cell SH-SY5Y is significantly better than that of NK 92 cells.

Example 7 Evaluation of Specific Lysis Acticiy of ROBO1M CAR-NK Cells on Breast Cancer Cells The specific lysis activity of ROBO1M CAR-NK cells on mammary gland cell lines of MCF-7, HCC1143, HCC1187, HCC1599, HCC1806 and HCC38. NK 92 cells were used as control. The experimental results were shown in FIG. 6a-6f.

The experimental results show that the specific lysis activity of ROBO1M-CAR NK cells on mammary gland cell lines of MCF-7, HCC1143, HCC1187, HCC1599, HCC1806 and HCC38 is significantly better than that of NK 92 cells.

The Anti ROBO1 CAR-NK cell provided in the present invention has specific lysis activity to various of cancer cells such as lung cancer cell line H1299, lung cancer cell line A549, pancreatic cancer cell line ASPC-1, hepatoma cell line HepG2, glioma cell line U87-MG, glioma cell SH-SY5Y, mammary gland cell line MCF-7, mammary gland cell line HCC1143, mammary gland cell line HCC1187, mammary gland cell line HCC1599, mammary gland cell line HCC1806 and mammary gland cell line HCC38, which provides hope for the treatment of cancer patients.

Example 8 Application of ROBO1M CAR-NK Cell in the Treatment of Breast Cancer I. Patient Situation The patient Wang, who was female and aged 55 years old. when she took a bath in June, 2016, she found a streak lump on the right side of the breast which cannot be moved by pushing, and accompanying with yellow odorous liquid overflowing from the nipple. There were multiple swollen lymph nodes in her right axilla, with no pain, no nausea and vomit, no dizziness, no headache or other discomfort.

In February, 2017, the patient went to the hospital because of waist pain. The CT of head and chest on Feb. 13, 2007 showed: 1. avity obstruction was found in right basal ganglia and inflammation was found in left upper frontal sinus and ethmoid sinus; 2. right breast lesion indicated right breast K with the right axillary lymph node metastasis; 3. multiple subpleural nodules were found in the upper lobe of the right lung, and fibrous foci was found in the lower lobe of the right lung; 4. calcification foci was found in the lower lobe of right lung, and fibrous foci was found in the tongue of left lung and the lower lobe of right lung, and a small amount of effusion was found in the right thoracic cavity; 5. multiple bone destructions were found in thoracic vertebrae, lumbar vertebrae, bilateral ribs inside of sacrum, bilateral iliac bone and pubic bone, considering metastasis and pathological fracture of right 7/10 rib, left third rib and left pubic bone; 6. enlargement was found in uterine body. The hospital local biopsy pathology in Feb. 14, 2017 showed: (right breast) invasive ductal carcinoma grade II. Immunology pathology: cancer cells E-cadherin (+), Ki-67 (+), about 10%, ER (+), strong, positive rate of about 90%, PR (−), Her2 (−), CK7 (+), P63 (−), CK5/6 (−). Combined with history and pathology, it was diagnosed as right breast invasive ductal carcinoma. The patient refused to take radiochemotherapy and was discharged from hospital.

In April 2017, the patient went to the hospital due to enlargement of lump. The CT reexamination of chest and abdomen on Apr. 11, 2017 showed: there was breast cancer with multiple metastases of spine and rib, multiple swollen lymph nodules in both armpits, multiple nodules in two lungs, considering metastasis. There are chronic bronchitis with infection in two lungs and bilateral pleural effusion. For symptomatic treatment, Yan Shu, Qiang Lin Tan and zoledronic acid and the like were administrated, but the effect was not good. Letrozole oral treatment was given on May $12^{th}$. On the second day of treatment, atrial fibrillation occurred, and improved after administration of goxin, betaloc and shexiang baoxin pills.

On May 17, 2017, the main symptoms included: palpitation, chest tightness, involuntary twitching of both lower limbs, limited lower limb movement, and obvious pain in the waist and back. Body examination results included: larger tumber in the right breast with the size of lox 7 cm, multiple ulceration on local skin, atrial fibrillation showed by electrocardiogram.

Complete PET-CT on May 19, 2017 showed: 1. Right breast lesion, increased FDG uptake, considering widespread metastases of double lung, multiple lymph nodes and multiple bone. 2. Inflammation in both lungs and bilateral pleural effusion. 3. The examination suggested multiple bone metastases all through the body, so zoledronic acid was used to protect bones. Patient could not tolerate systemic intravenous chemotherapy because of atrial fibrillation. The patient and her family refused to accept systemic chemotherapy and considered to accept immunologic cell therapy after their discussion.

II. Treatment Design

Figure 10:
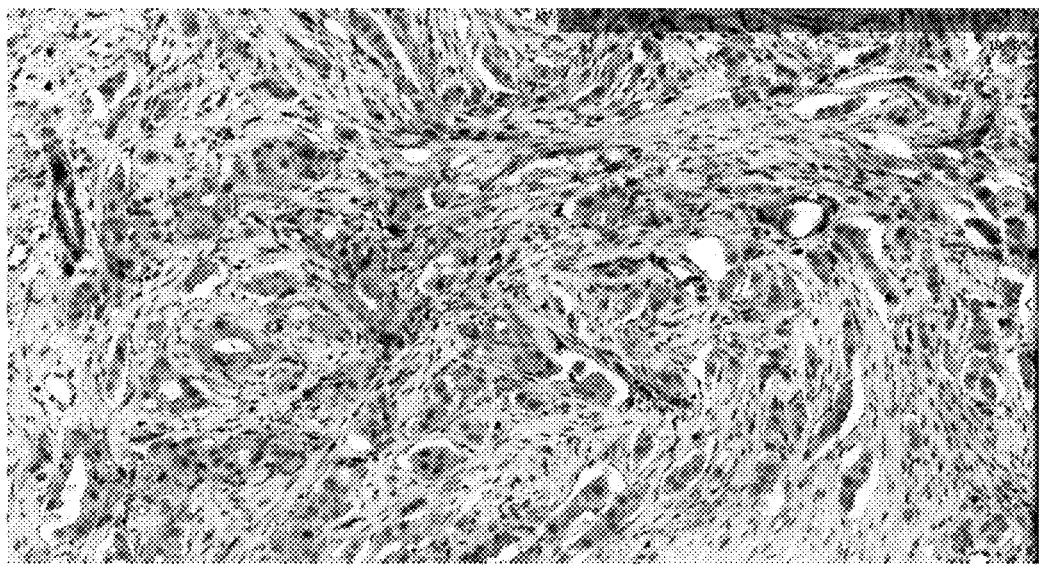
FIG. 10 shows a result of histochemical detection of breast cancer patients provided in Example 8.
Figure 11:
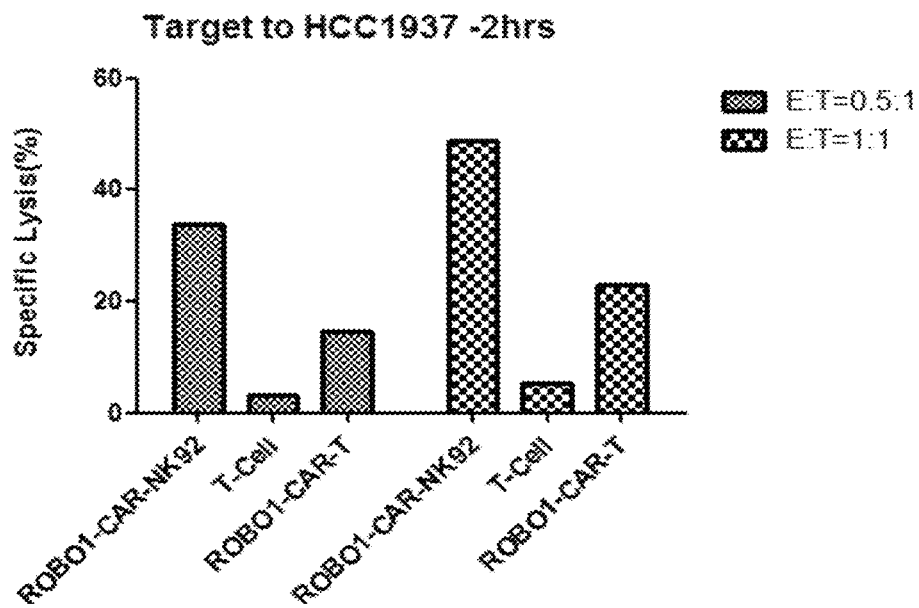
FIG. 11 shows the comparative result between the specific lysis activity of ROBO1M CAR-NK cells and ROBO1M CAR-T cells on HCC1937 cells provided in comparative Example 1.
Figure 12:
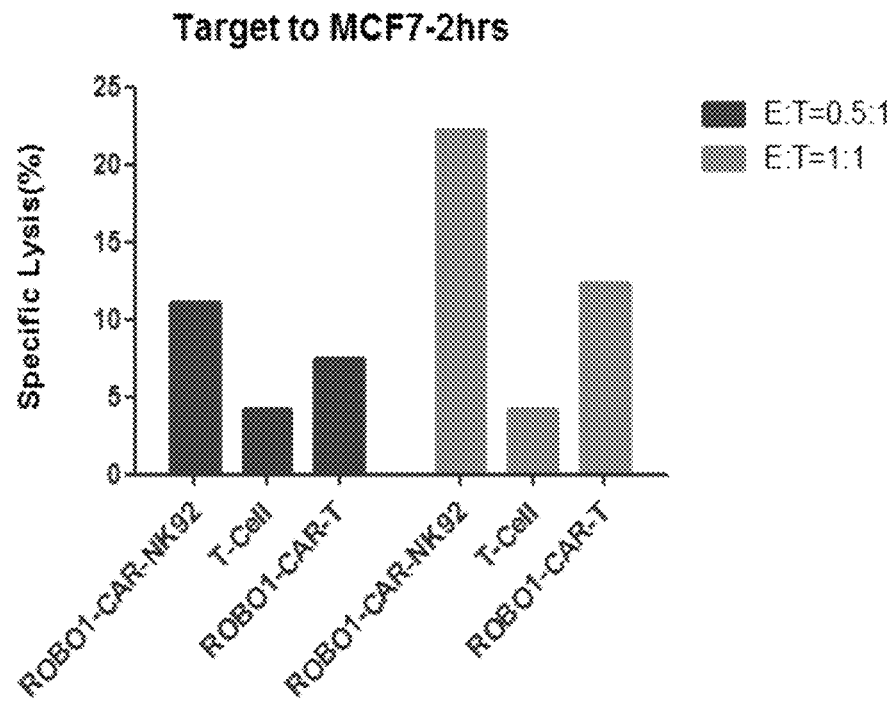
FIG. 12 shows the comparative result between the specific lysis activity of ROBO1M CAR-NK cells and ROBO1M CAR-T cells onMCF7 cells provided in comparative Example 1.
Figure 13:
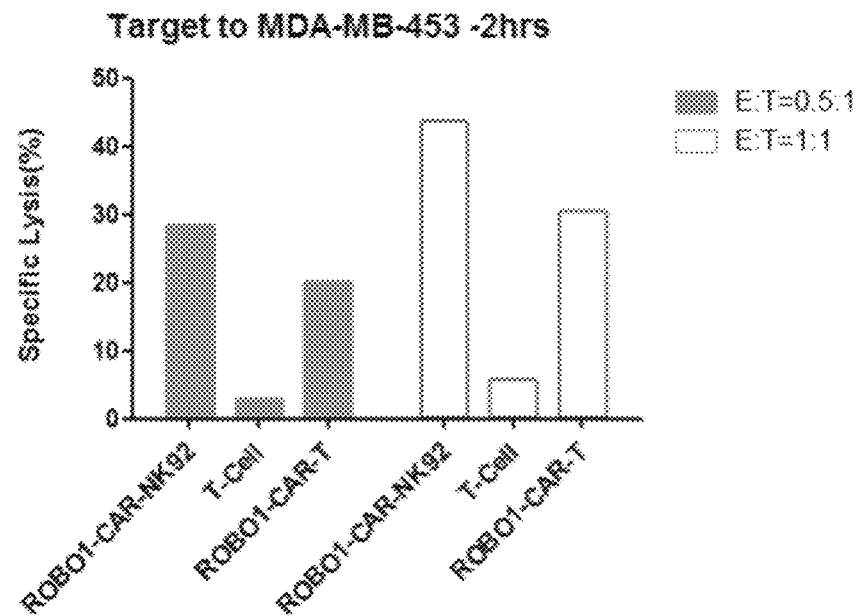
FIG. 13 shows the comparative result between the specific lysis activity of ROBO1M CAR-NK cells and ROBO1M CAR-T cells on MDA-MB-453 cells provided in comparative Example 1.
Figure 14:
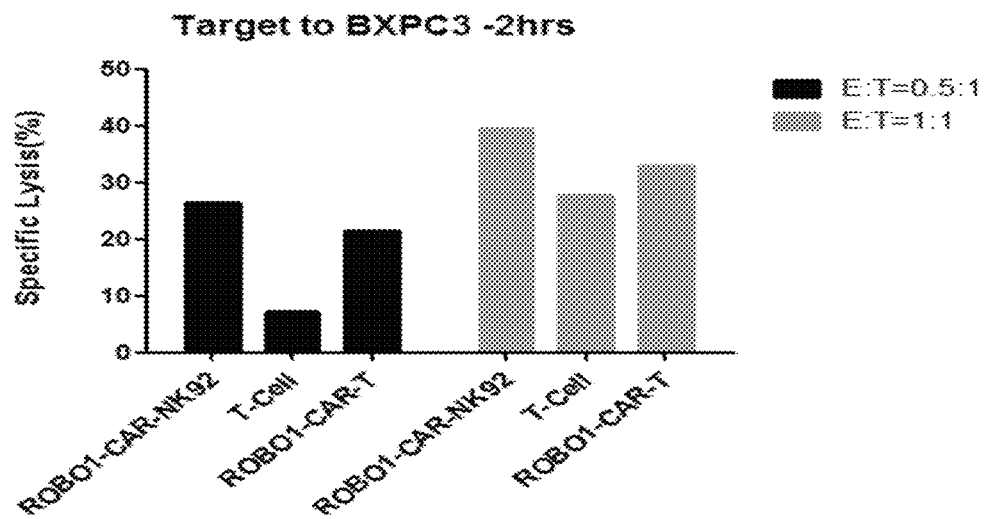
FIG. 14 shows the comparative result between the specific lysis activity of ROBO1M CAR-NK cells and ROBO1M CAR-T cells on BXPC3 cells provided in comparative Example 1.

Before the treatment design, the expression of ROBO1 target was detected by pathological histochemistry, and the results were shown in FIG. 10. It was positive, so Robo1M CAR-NK cells could be used in the treatment. In view of the serious local lesions and bone metastases, a prior direct injection into the tumor tissue and a later systemic treatment were designed. Patients received direct injection of Robo1M CAR-NK cells 2 times a week, 1 day interval. The number of initial injections was $1\times10^9$ cells/time, and if there was no adverse reaction, the number was increased to $2\times10^9$ cells/time. In order to reduce the adverse reactions related to infusion, dexamethasone and promethazine hydrochloride were given before the injection of cells, and if the tolerance was good, the dosage of dexamethasone should be reduced or canceled. If the patient respond after the local injection, systemic treatment should be given.

III. Therapy Process

Figure 9:
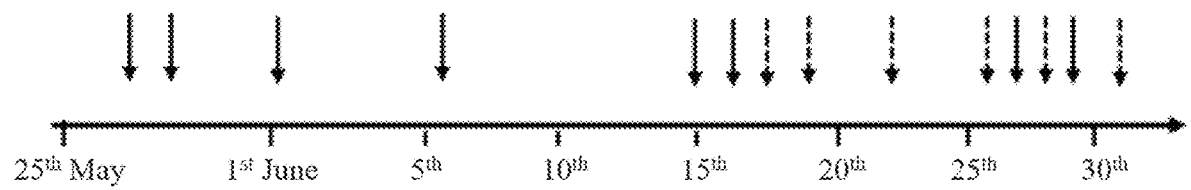
FIG. 9 shows a schematic diagram of the therapy process using Robo1M CAR-NK cells provided in Example 8.

From May 25, 2017 to Jun. 29, 2017, the patient received 8 direct injections of Robo1M CAR-NK cell to tumor site, wherein 2 times are $1\times10^9$ cells/time and 6 times are $2\times10^9$ cells/time. From June $17^{th}$ onwards, patients began receiving intravenous infusion of cells, $2\times10^9$ cells per time, 3 times one week, 1 day interval, 5 times in total until June $29^{th}$. The therapy process is shown in FIG. 9, which is a schematic diagram of the therapy process using Robo1M CAR-NK cells. In it, the solid arrow refers to directly injecting into the tumor tissue, and the dotted arrow refers to intravenous infusion.

IV. Treatment Outcome

Two injections of Robo1M CAR-NK cells locally into the right breast were performed on May 25th and June 6th. The right breast lump was significantly reduced, narrowed to 6×5 cm size, and the local rupture of the breast improved significantly, suggesting the treatment was effective.

On June 12th, the CT reexamination of head showed no abnormality, and the enhanced CT of chest and abdomen showed stable condition.

From June 15th onwards, both local and Systemic treatments using Robo1M CAR-NK cells were performed for more than 1 month, turning out that the right breast lump was obviously reduced to 2×3 cm and the ulceration site basically healed.

Figure 7:
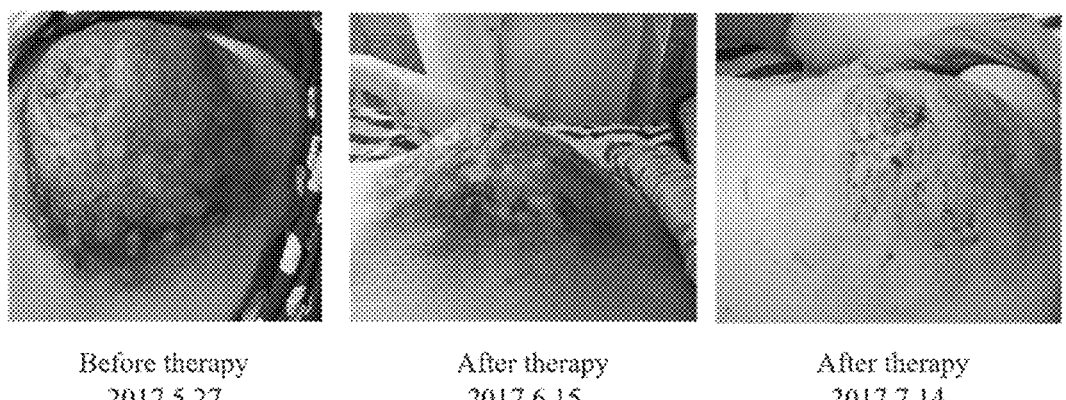
FIG. 7 shows a comparative result between before and after the treatment of breast cancer by Robo1M CAR-NK cell therapy provided in Example 8.

On July 17th, the chest enhanced CT showed that the pleural effusion was significantly reduced. The patients had no palpitation or chest tightness, basically relieved shoulder pain and significantly reduced right breast lump compared with that in May (as shown in FIG. 7), indicating that the condition was stable and gradually improved.

According to the domestic and international reports, in the treatment of cancer with CAR-T cells, it could happen rapid increase of cytokines such as IL-6, causing the phenomenon of cytokine release syndrome, and it could endanger the lives of patients when serious. Therefore, the experiment further detected the changes of cytokines in the patient's body during the treatment of tumors with Robo1M CAR-NK cells, and the results were shown in FIG. 8a and FIG. 8b.

Figure 8A:
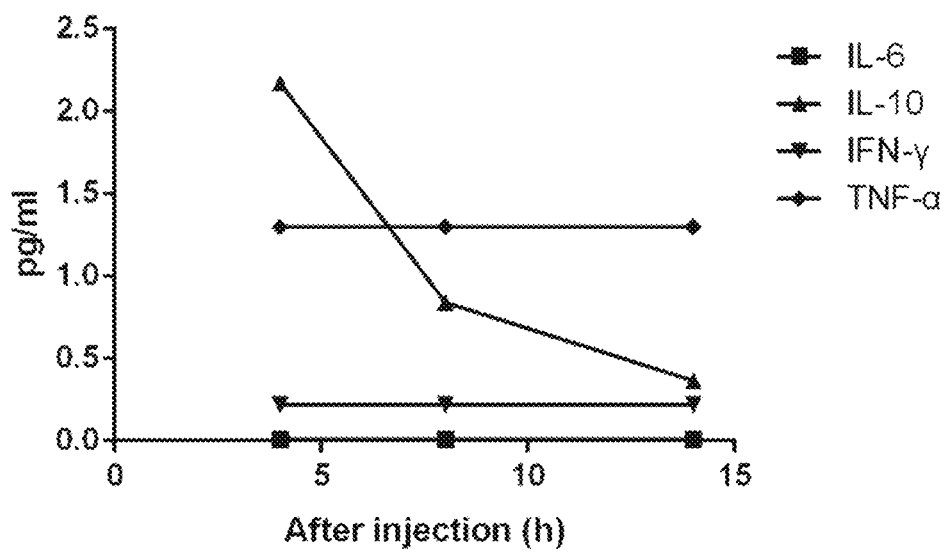
FIG. 8a shows a detection result of cytokine after direct injection of Robo1M CAR-NK cells into the lesion provided in Example 8.
Figure 8B:
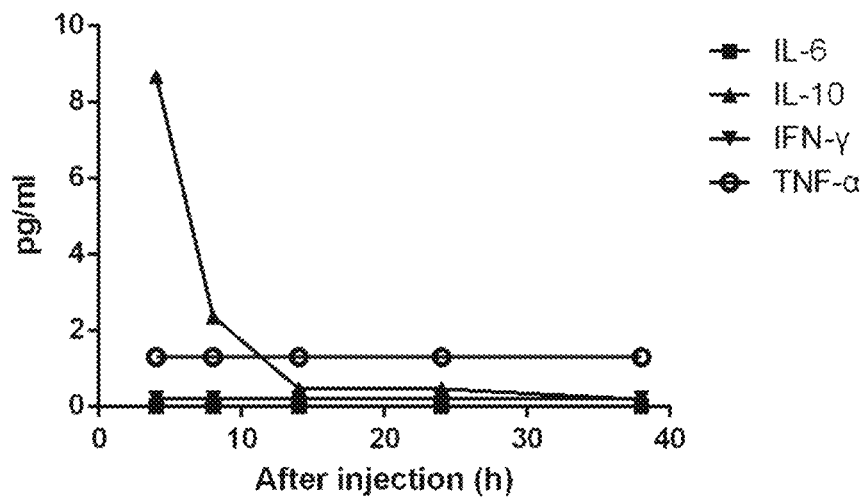
FIG. 8b shows a detection result of cytokine after intravenous infusion of Robo1M CAR-NK cells provided in Example 8.

The results of FIG. 8a and FIG. 8b showed that no matter Robo1M CAR-NK cells were injected locally into the tumor or injected with blood, only a single increase in IL-10 was observed in the patient's body, and no significant changes of IL-6 or other cytokines were observed. Combined with the good condition of the patients during the treatment, it indicated that the product of Robo1M CAR-NK cells has good safety, which could avoid adverse effects such as cytokine release syndrome and so on, and could effectively treat tumors and improved the survival rate.

Comparative Example 1 Comparison of the Specific Lysis Activity of ROBO1 CAR-T Cells and ROBO1M CAR-NK Cells The specific lysis activity of ROBO1 CAR-T cells and ROBO1M CAR-NK cells on various tumor cell lines using T cells as control were detected by CFSE staining method. The tumor cell lines include: breast cancer cell lines including HCC1937, MCF7 and MDA-MB-453, and pancreatic cancer cell line BXPC3. The experimental process included:

(1) The target cells should be treated in advance. It was added with 1 μL of CFSE per $1 \times 10^6$ cells, incubated for 15 min in dark incubator, terminated by 10% BSA, and cleaned twice with PBS. 500 μL of prepared tumor cell suspension ($8 \times 10^4$/well) was add into 24-well plate and pre-incubated in incubator for 12 h.

(2) 5000 μL of effector cells was added according to the ratios of effector cells to target cells were 0.5:1 and 1:1. Three parallel wells were placed in each experiment. The effector cells are incubated with target cells for 4 hours.

(3) After 4 hours, the supernatant was transferred to 1.5 EP tube. In the meantime, 200 μL of pancreatin was added to each well. After digesting for 1 min, the cells were blown with the corresponding supernatant, centrifuged and resuspended with PBS. 1 μL of 7-AAD was added, incubated for 15 min in dark, and detected by machine.

(4) Specific lysis activity=(target cell killing rate–spontaneous death rate)/(1–spontaneous death rate)×100%;

The experimental results of specific lysis activity of ROBO1 CAR-T cells and ROBO1 CAR-NK cells on tumor in vitro are shown in FIG. 11 to FIG. 14.

The experimental results in FIG. 11 to FIG. 14 confirm that ROBO1 CAR-T cells and ROBO1M CAR-NK cells have strong specific lysis activity on breast cancer cell lines including HCC1937, MCF7 and MDA-MB-453 and pancreatic cancer cell line BXPC3, and their effects are better than those of ordinary T cells.

In addition, it can be seen from FIG. 11 to FIG. 14 that the specific lysis activity of ROBO1M CAR-NK is obviously better than that of ROBO1 CAR-T cells, and ROBO1M CAR-NK cells can kill tumors more effectively.

In summary, the ROBO1 CAR-NK cells provided in the present invention can specifically kill tumor cells by using ROBO1 antibody for the construction of CAR-NK cells and using ROBO1 molecules as target antigens; it can be used as a therapeutic agent for tumor diseases, for the treatment of tumor with highly expressing ROBO1, without harmful phenomena such as cytokine release syndrome, thus providing new treatments for the tumors which are ineffective in traditional surgery, chemotherapy and radiotherapy; it can improve its targeting ability by transforming NK92 cells with CAR, moreover, greatly improve its anti-tumor ability while increasing t anti-tumor targeting sites ROBO1; in addition, the ROBO1 CAR-NK cells has a significantly better specific lysis activity compared with ROBO1 CAR-T cells, and can be more effective in killing tumors; that is to say, by transforming NK92 cells through engaging CAR, the ROBO1 CAR-NK cells constructed by the present invention can not only be significantly improved in its targeting ability, but also get higher safety, lower toxicity and side effects and lower costs by transforming NK cells; and because of the coefficient of NK cells, CAR and anti-tumor target sites ROBO1, the specific lysis activity is good and obviously better than ROBO1 CAR-T cells.

The above mentioned is only preferable embodiments of the present invention, and cannot be used to restrict the invention. Any modification, equivalent replacement and the like within the spirit and principles of the present invention should be included in the scope of protection of the present invention.

What is claimed is:

1. A nucleotide sequence for encoding a chimeric antigen receptor, which comprises an antigen binding domain, a transmembrane domain and a costimulatory signal transduction region, wherein the antigen binding domain is an antibody or an antigen binding fragment thereof specifically binding to the FN3 domain of ROBO1, and activate NK cells through the transmembrane domain and the costimulatory signal transduction region;

and the chimeric antigen receptor is a fusion protein with a structure of ScFV-CD8-4-1BB-CD3ζ, and the amino acids sequence of the fusion protein ScFV-CD8-4-1BB-CD3ζ is shown in SEQ ID NO: 3.

2. The nucleotide sequence for encoding a chimeric antigen receptor of claim 1, wherein the encoding nucleotide sequence of the fusion protein ScFV-CD8-4-1BB-CD3ζ is shown in SEQ ID NO: 4.

3. A ROBO1 CAR-NK cell, which can express chimeric antigen receptor, wherein the chimeric antigen receptor comprises an antigen binding domain, a transmembrane domain and a costimulatory signal transduction region, and the antigen binding domain is an antibody or an antigen binding fragment thereof specifically binding to the FN3 domain of ROBO1, and can activate NK cells through the transmembrane domain and the costimulatory signal transduction region;

and the chimeric antigen receptor is a fusion protein with a structure of ScFV-CD8-4-1BB-CD3ζ, and the amino acids sequence of the fusion protein ScFV-CD8-4-1BB-CD3ζ is shown in SEQ ID NO: 3.

4. The ROBO1 CAR-NK cell of claim 3, wherein the nucleotide sequences of the fusion protein ScFV-CD8-4-1BB-CD3ζ is shown in SEQ ID NO: 4.

5. The ROBO1 CAR-NK cell of claim 3, wherein the ROBO1 CAR-NK cell can effectively destroy or kill lung cancer cell line, pancreatic cancer cell line, hepatoma cell line, glioma cell line, mammary gland cell line, colon cancer cell line or prostate cancer cell line.

6. The ROBO1 CAR-NK cell of claim 5, wherein the cell lung cancer cell line is H1299 or A549, the pancreatic cancer cell line is ASPC-1 or BXPC3, the hepatoma cell line is HepG2, the glioma cell line is U87-MG or SH-SY5Y, or the breast cancer cell line is MCF-7, HCC1143, HCC1187, HCC1599, HCC1806, HCC38, HCC1937 or MDA-MB-453.

7. A pharmaceutical composition, characterized in that the pharmaceutical composition comprises an effective therapeutic amount of the ROBO1 CAR-NK cell of claim 3.

8. The pharmaceutical composition of claim 7, wherein the pharmaceutical composition also includes pharmaceutically acceptable adjuvants, the dosage form of the pharmaceutical composition is aqua.

9. A method for treating cancer by providing the ROBO1 CAR-NK cell of claim 3 to a subject in need thereof, wherein the cancer is a tumor highly expressing ROBO1 molecules.

10. The method of claim 9, wherein the cancer is liver cancer, breast cancer, colon cancer, pancreatic cancer, prostate cancer, glioma, or lung cancer.

11. The method of claim 9, wherein the administration mode of the drugs containing ROBO1 CAR-NK cells is intratumoral injection, intravenous injection, intrathoracic injection or local intervention.

* * * * *